US008530206B2

(12) United States Patent
Develter et al.

(10) Patent No.: US 8,530,206 B2
(45) Date of Patent: Sep. 10, 2013

(54) METHOD FOR THE PRODUCTION OF MEDIUM-CHAIN SOPHOROLIPIDS

(75) Inventors: Dirk Develter, Maldegem (BE); Steve Fleurackers, Deurne (BE); Inge Van Bogaert, Laarne (BE)

(73) Assignee: Ecover Coordination Center N.V., Antwerp (BE)

( * ) Notice: Subject to any disclaimer, the term of this patent is extended or adjusted under 35 U.S.C. 154(b) by 115 days.

(21) Appl. No.: 12/994,077

(22) PCT Filed: May 20, 2009

(86) PCT No.: PCT/EP2009/056190
§ 371 (c)(1),
(2), (4) Date: Feb. 14, 2011

(87) PCT Pub. No.: WO2009/141407
PCT Pub. Date: Nov. 26, 2009

(65) Prior Publication Data
US 2011/0136110 A1 Jun. 9, 2011

(30) Foreign Application Priority Data
May 21, 2008 (EP) .................................... 08156696

(51) Int. Cl.
C12P 7/62 (2006.01)
C12P 7/64 (2006.01)

(52) U.S. Cl.
USPC ....... 435/134; 435/135; 435/254.22; 435/490

(58) Field of Classification Search
USPC .............................. 435/134, 135, 254.22, 490
See application file for complete search history.

(56) References Cited

U.S. PATENT DOCUMENTS
5,254,466 A * 10/1993 Picataggio et al. ........... 435/142

FOREIGN PATENT DOCUMENTS
WO 91/06660 A 5/1991
WO 99/24448 A 5/1999

OTHER PUBLICATIONS

Ferdinandusse et al.; Identification of the peroxisomal Beta-oxidation enzymes involved in the degradation of long-chain dicarboxylic acids; Journal of Lipid Research; vol. 45, pp. 1104-1111; published Apr. 1, 2004.*
Kurtzman et al.; Production of sophorolipid biosurfactants by multiple species of the *Starmerella* (*Candida*) *bombicola* yeast clade; FEMS Microbiology Letters; vol. 311; pp. 140-146 (2010).*
Banat; Biosurfactants production and possible uses in microbial enhanced oil recovery and oil pollution remediation: a review; Bioresource Technology; vol. 51; pp. 1-12 (1995).*
Van Bogaert, Inge N A et al: "Development of a transformation and selection system for the glycolipid-producing yeast *Candida bombicola*" Yeast, vol. 25, No. 4, Apr. 1, 2008, pp. 273-278.
Inge N A Van Bogaert et al: "Microbial production and application of sophorolipids" Applied Microbiology and Biotechnology, Springer, Berlin, DE, vol. 76, No. 1, May 3, 2007, pp. 23-34.
Saito M et al: "Accumulation of glycolipids in mutant Chinese hamster ovary cells (Z65) with defective peroxisomal assembly and comparison of the metabolic rate of glycosphingolipids between Z65 cells and wild-type CHO-KI cells" Biochimica and Biophysica Acta. Molecular and Cell Biology oflipids, Elsevier, Amsterdam, NL, vol. 1438, No. 1, Apr. 19, 1999, pp. 55-62.
Rau U et al: "Sophorolipids: a source for novel compounds" Industrial Crops and Products, Elsevier, NL, vol. 13, Jan. 1, 2001, pp. 85-92.
Van Bogaert, Inge N A et al: "Knocking out the MFE-2 gene of *Candida bombicola* leads to improved medium-chain sophorolipid production" FEMS Yeast Research, vol. 9, No. 4, Jun. 2009, pp. 610-617.
International Search Report completed Sep. 24, 2010 by the European Patent Office for International Application No. PCT/EP2009/056190.
Written Opinion completed Sep. 23, 2010 by the European Patent Office for International Application No. PCT/EP2009/056190.

* cited by examiner

*Primary Examiner* — Michele K Joike
*Assistant Examiner* — Antonio Galisteo Gonzalez
(74) *Attorney, Agent, or Firm* — Knobbe, Martens, Olson & Bear LLP

(57) ABSTRACT

The MFE2 gene of a microorganism capable of producing glycolipids, such as, but not limited to *C. bombicola* is disrupted with the purpose of blocking the beta-oxidation pathway in the strain. Fermentation of a such strain having such disrupted genes on primary or secondary alcohols or diols, preferably on primary alcohols produces short chained glycolipids in high yield and purity.

21 Claims, 5 Drawing Sheets

METHOD FOR THE PRODUCTION OF MEDIUM-CHAIN SOPHOROLIPIDS

CROSS-REFERENCE TO RELATED APPLICATIONS

This application is a §371 national stage entry of International Application No. PCT/EP2009/056190, filed May 20, 2009, which claims priority to European Patent Application 08156696.0, filed May 21, 2008, the entire contents of which are incorporated herein by reference.

FIELD OF THE INVENTION

The present invention relates to a method for producing glycolipids, in particular sophorolipids with medium length hydrocarbon chains.

The present invention also relates to a process for the site-specific modification of the genome of a host strain of a glycolipids producing micro-organism with the purpose of optimising the strain for the production of medium length hydrocarbon chain glycolipids, preferably sophorolipids.

BACKGROUND OF THE INVENTION

The use of glycolipid biosurfactants in detergents is well known in the art. Glycolipid biosurfactants include rhamnolipids, sophorolipids, cellobioselipids, trehaloselipids, mannosyl erythritol lipids and (bio)chemical modifications thereof. Glycolipid based biosurfactants are understood to comprise those surfactants that have been obtained through microbial cultivation and consist of carbohydrates bound to aliphatic acids or aliphatic hydroxyl acids through glycosidation or acylation. They offer the advantage of being naturally produced molecules that can be produced through microbial cultivation by feeding renewable raw materials and of being fully degradable after use.

Sophorolipids are one of the most promising glycolipids known, one reason being their high production yield and ease of recovery from the microbial cultivation. Several *Candida* species, a.o. *Candida (Starmerela) bombicola* (formerly *Torulopsis bombicola*), *Candida apicola* (formerly *Torulopsis magnoliae* and *Torulopsis apicola*) and *Rhodotorula bogoriensis*, *Wickerhamiella domericqiae* are known to produce sophorolipids in large amounts from various substrates such as carbohydrates, vegetable oils, animal fats and n-alkanes. Sophorolipid production mainly takes place during the stationary phase because of nitrogen limitation. It appears to be enhanced when providing simultaneously hydrophilic (e.g. glucose) and hydrophobic (e.g. fatty acids) substrate to *Candida* species. *Candida bombicola* for example produces a complex mixture of 22 structurally different sophorolipids from either glucose and or an oily substrate, preferably C16 to C18 alkanes, fatty acids or their esters. The main compounds produced are the lactonic and the acidic form typically in the ratios of 75 and 25 w/w. A typical hydroxyl fatty acid distribution incorporated in non, mono- and diacetylated sophorolipids either in their free acid or lactonic form is for example disclosed in FR2779057:

TABLE 1

| Type | Hydroxy fatty acid | Wt. % |
|---|---|---|
| C16:0 | 15-OH hexadecanoic | 1.5 |
| C16:0 | 16-OH hexadecanoic | 2 |
| C18:0 | 17-OH octadecanoic | 3.5 |

TABLE 1-continued

| Type | Hydroxy fatty acid | Wt. % |
|---|---|---|
| C18:1 | 17-OH octadecenoic | 60 |
| C18:1 | 18-OH octadecenoic | 12 |
| C18:2 | 17-OH octadecadienoic | 7 |
| C18:2 | 18-OH octadecadienoic | 14 |

Sophorolipids find numerous applications for example in preventing and curing dandruff and body odor attributed to bacteriostatic properties, as disclosed by EP-A-1.082.097; as therapeutically active substances or cosmetic products, in particular skin treatment as disclosed by EP-A-835.118; and for their antifungal properties disclosed by US-A-2005/0164955. EP-A-820.273 discloses that sophorolipids are non-irritant to the skin, weakly irritant to the eyes only and that they show anti-inflammatory as well as elastase inhibiting activity. Other uses of sophorolipids include their use as the sole surfactant in washing and cleaning applications such as disclosed in U.S. Pat. No. 6,433,152. According to EP-A-1.445.302 mixtures of sophorolipids show synergistic activity in laundry and hard surface cleaning applications. EP-A-499.434 discloses to combine sophorolipids with lamellar, usually ethoxylated non-ionic surfactants in washing and cleaning applications. DE-A-19600743 discloses manual dishwashing formulations based on sophorolipids and other glycolipids combined with high foaming surfactants.

However, the physicochemical properties of sophorolipids form an important limitation to their applicability. In this respect it is mentioned that the lactonic form of the sophorolipids is hardly water soluble, it is insoluble in acidic environment, it is spontaneously deacetylated in alkaline pH and upon deacetylation the pH reduces to approximately 6. Fully de-acetylated acidic sophorolipids appear to lose a substantial part of their surface activity with respect to the di-acetylated lactonic form of crude sophorolipids. Shorter-chained sophorolipids are presumed to decrease surface tension more effectively than the known long chain C16-C22 sophorolipids. Therefore several attempts have been made to find an efficient process for their production. Whereas, *Candida bombicola* and its most commonly used strain (ATCC 22214) have been found capable of readily fermenting C16 and C18 chains and of incorporating them into the glycolipids, shorter hydrocarbon chain precursors C10-C14 were found to be hardly incorporated by the micro-organism: they were assimilated instead. C15-sophorolipids could only be obtained in unsatisfactory yields of below 40% by Jones and Howe (1968), by offering a wide variety of expensive C15 substrates to *Torulopsis gropengiesseri*. Pentadecanoic acid proved to be too short for appreciable hydroxylation, which is an essential step in sophorolipid production by the micro-organism, and 12-hydroxyoctadecanoic acid did not react because the hydroxyl group is too close to the reaction site.

Traces of a C14 component could only be detected when a glucose/tetradecane mixture was used as hydrocarbon source. According to the teaching of U.S. Pat. No. 6,433,152 short chain 3-alkanols, 4-alkanols and 2, 3 and 4-alkanols could be converted into short chain sophorolipids with the envisaged chain length, provided the conversion was carried out under reduced oxygen concentrations and with an exceptionally high glucose feed. However, the yield was only between 3-17 g/l, of which only 41-85% had the envisaged short chain length. Although U.S. Pat. No. 6,433,152 claims incorporation of the easily obtainable and cost-effective 1-alcohols, no examples are given or yields specified. It therefore seems likely that 1-alcohols do not form a useful source for the production of short-chain sophorolipids, as these are first converted into the corresponding acids before they are transformed into glycolipids rather than being glycosidically bound at the hydroxyl group (Jones et al, 1968). According to the disclosure of DE19518982.5 *Candida* species are capable of converting secondary alcohols or ketones to non-cyclic sophorose lipids with surface active properties. The yields amount to approximately 20 g/l of C12-C14 sophorolipids, 75-85% of which has the desired chain length. 7% was converted into a fatty diol. However, the low yield, combined with the impurity of the end product which is a mixture containing 10% of standard C18 sophorolipids and the fact that secondary alcohols are expensive, render this process unattractive.

In most *Candida* species, substrates having a hydrocarbon chain of more than 18 carbon atoms, are first reduced in chain length by one or more units of two carbon atoms and only thereafter hydroxylated, thus yielding C16 or C18 hydroxy fatty acids with the OH group on the penultimate carbon atom (Tulloch, Spencer and Gorin 1962).

Van Bogaert et al (2007) describe the cloning, characterisation and functionality of the orotidine-5'-phosphate decarboxylase gene (URA3) in *Candida bombicola*.

DESCRIPTION OF THE INVENTION

Figure 1:
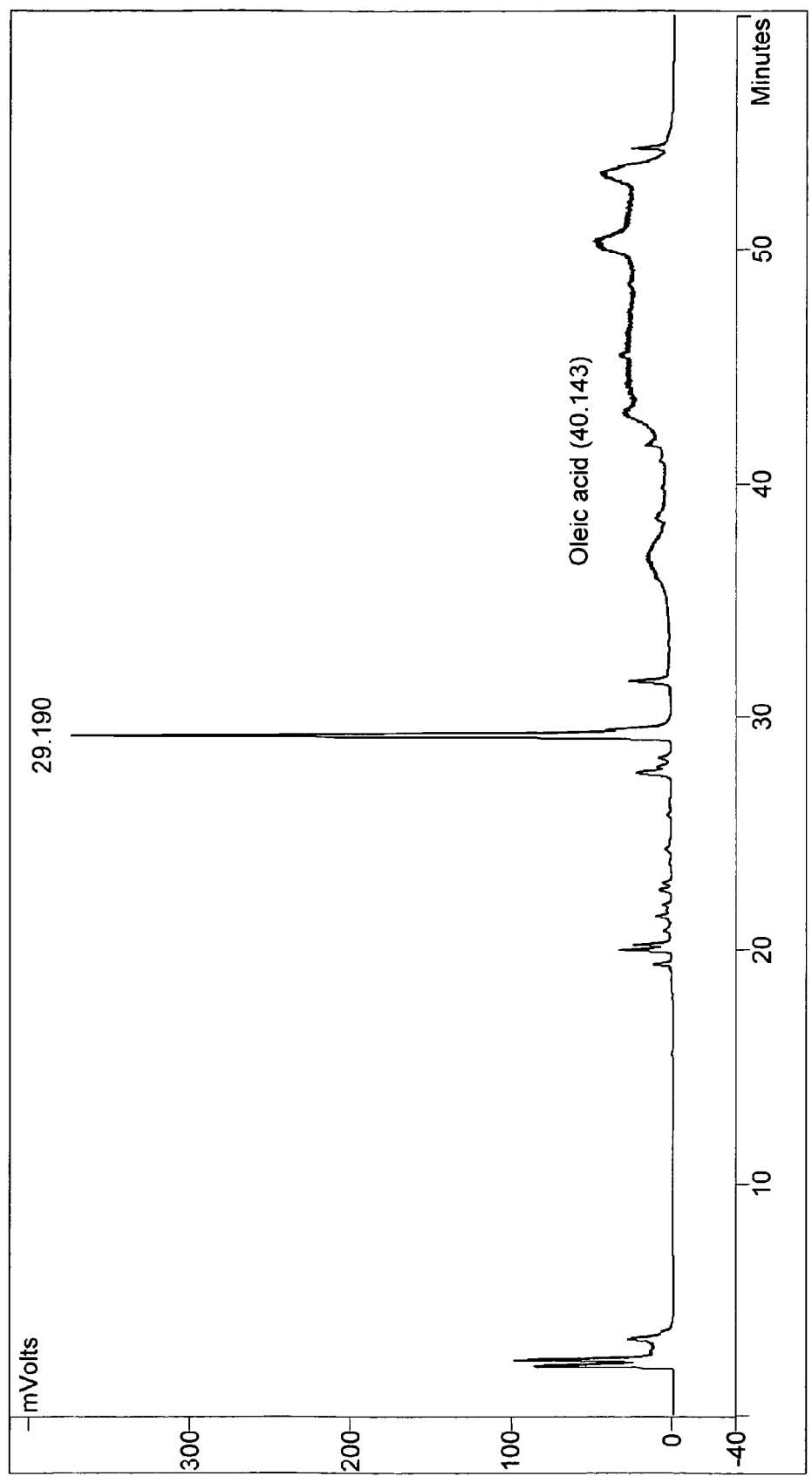
FIG. 1: Sophorolipids from wild type *Candida* grown on rapeseed oil (wild type Sophorolipids at 29.9 min).

There is thus a need to a process with which shorter-chained glycolipids, in particular sophorolipids may be produced at higher yields and selectivity than could be achieved up to now, as those are presumed to decrease surface tension more effectively than the known long chain C16-C22 glycolipids.

In particular, there is a need for a process with which medium-chain glycolipids or an acetylated derivative thereof, can be produced at an acceptable yield, wherein the process shows a sufficient selectivity towards the desired glycolipid. More particularly, there is a need for a process with which glycolipids or an acetylated derivative thereof, more in particular glycolipids with a hydrocarbon chain length of C14 or less, preferably a hydrocarbon chain length of between 8-14 carbon atoms, can be produced at an acceptable yield, and a sufficient selectivity towards the desired glycolipid, in particular sophorolipid.

It is therefore the object of the present invention to provide a process for producing medium-chain glycolipids, in particular glycolipids with a hydrocarbon chain length of 14 or less, more particularly with a hydrocarbon chain length of between 8 and 14 carbon atoms, at an acceptable yield, and a selectivity towards the desired glycolipid which is sufficiently high.

It is also an object of the present invention to provide a micro-organism which is capable of producing such glycolipids at an acceptable yield and selectivity, and a process for producing such a micro-organism.

This object is achieved according to the present invention when with the technical features of the characterizing portion of the first claim.

Thereto, the present invention provides a process for the site-specific modification of the genome of a host strain of a glycolipids producing micro-organism, which process comprises the steps of:

(1) transforming the host by disrupting through homologous recombination, at least one target gene encoding for at least one enzyme in the β-oxidation pathway
(2) selecting the thus produced transformants by the ability of the transformants to grow in a selective medium.

Preferably the process of the present invention for the site-specific modification of the genome of a host strain of a glycolipids producing micro-organism, comprises the step of transforming the host by disrupting through homologous recombination at least one target gene encoding for enoyl-CoA hydratase and 3-hydroxyacyl-CoA dehydrogenase in the β-oxidation pathway.

More preferably the process of this invention is characterised in that the process comprises the step of transforming the host by disrupting at least the MFE2 gene.

A further preferred embodiment of the process for the site-specific modification of the genome of a glycolipids producing micro-organism the present invention is characterised in that it comprises the steps of:

(1) transforming the host by disrupting through homologous recombination a target gene selected from the group consisting of the MFE2 and combinations thereof with a DNA fragment comprised of a selectable marker gene;
(2) selecting the thus produced transformants by the ability of the transformants to grow in a selective medium.

Preferably the marker gene is selected from the group of an auxotrophic marker, antibiotic marker.

Preferably, the selectable marker gene is flanked on both ends by DNA sequences having homology to the target gene or having homology to DNA sequences flanking a chromosomal target gene. One aspect of the present invention relates to a process for the site-specific modification of the *C. bombicola* genome, comprising transforming a *C. bombicola* host cell with a linear DNA fragment comprised of a selectable marker gene, wherein said selectable marker gene is flanked on both ends by DNA sequences having homology to a chromosomal target gene or having homology to DNA sequences flanking a chromosomal target gene.

Preferably the DNA fragment is a selectable marker gene flanked on both ends by a MFE2 sequence of at least 100 base pairs, preferably at least 500 base pairs, more preferably at least 1000 base pairs. The inventors have namely found that the amount of transformants that may be obtained, significantly increases when using a fragment which on both ends is flanked with at least 1000 base pairs.

According to the teaching of Brachmann et al, 1998 knocking out genes in *S. cerevisiae* is relatively simple. Since *S. cerevisiae* laboratory strains are efficient in homologues recombination, events of double cross-over or gene replacement occur frequently enough to yield the right transformants. However, this strategy failed for *C. Bombicola* and did not yield proper transformants. The inventors have now found that a sufficient amount of transformants could only be obtained provided the selectable marker gene is flanked on both ends by a MFE2 sequence of at least 100 base pairs.

Preferably the selectable marker gene is the URA3A gene.

Preferred host micro-organisms include *Candida (Starmerela) bombicola* (formerly *Torulopsis bombicola*), *Candida apicola* (formerly *Torulopsis magnoliae* and *Torulopsis apicola*) and *Rhodotorula bogoriensis, Wickerhamiella domericqiae*, the more preferred host micro-organism being *Candida Bombicola* ATCC22214.

When analysing sophorolipid production by existing *C. bombicola* cultures, the inventors have observed that when *C. bombicola* is cultivated with a less favourable substrate for sophorolipid production such as shorter primary alcohols, part of the substrate is not converted into sophorolipids but is metabolized in the β-oxidation pathway instead. The analysis by the inventors also learned a feed of fatty acids is converted to acyl-CoA by acyl-CoA-synthetase before it enters the actual β-oxidation pathway, and is then transported into the peroxisomes. The analysis by the inventors further learned that the β-oxidation is a cyclic pathway, which comprises four reactions. After every cycle an acetyl-CoA molecule and an acyl-CoA lacking two carbon atoms are obtained, this until in the final cycle two acetyl-CoA molecules are released.

The first reaction of the β-oxidation pathway is performed by acyl-CoA dehydrogenase. In some yeast species, multiple acyl-CoA dehydrogenase genes or PDX genes occur, which are all functionally translated into isozymes. *C. maltosa* for example has two such genes (and *C. tropicalis* three. In the genome of *Yarrowia lipolytica*, even five PDX genes were found some of them show activity against short-chain fatty acids (with a chain length of less than 6 carbon atoms), others against long-chain fatty acids (with a chain length of more than 18 carbon atoms) and some are active against molecules of all chain lengths. According to the teaching of U.S. Pat. No. 5,254,466, in order to completely shut down the β-oxidation pathway, a quadruple mutant has to be created. From this the inventors conclude that the number of PDX genes is variable, but that there is a bigger chance to the occurrence of isozymes for yeasts that readily metabolize alkanes or fatty acids. *C. bombicola* belongs to this latter group, and therefore it can be expected that in this species multiple PDX genes are active as well. From this, the inventors conclude that creation of a mutant blocked in its β-oxidation by knocking out PDX genes is not very convenient, since all PDX genes must be isolated and possibly multiple deletions must be made.

The inventors have further observed that the second step of the β-oxidation pathway which involves a hydration step and the third step of the β-oxidation pathway which involves a second dehydrogenation, are performed by one and the same enzyme in eukaryotic organisms: the so called multifunctional enzyme. Contrary to mammals, yeasts only possess MFE-2 and until now there is no evidence for the presence of isozymes in any yeast or fungal species. Therefore, the MFE-2 from *C. bombicola* is considered as an attractive target for gene disruption. It is expected that disabling of the gene would permit simultaneous inhibition of two biochemical reactions.

The last reaction of the β-oxidation cycle is the thiolytical cleavage. As in the genome of *C. tropicalis* four isozymes with different activities and specificities were found, only with double mutants β-oxidation could be inhibited (Kanayama et al, 1998). As it is likely that also in *C. bombicola* several isozymes are present, targeting of the thiolytical cleavage for blocking the β-oxidation pathway, seems less favourable.

Based on this analysis, the inventors came to the conclusion that an optimum improvement of the glycolipid production based on specialty substrates could be achieved by eliminating the competing β-oxidation pathway either by chemical or by genetic inhibition.

Experiments with chemical inhibitors of the β-oxidation added to the medium (e.g. bromobutyric acid) did not result in better use of the substrate. Either the chemicals were not active against the yeast pathway or could not perform properly due to the long fermentation period at low pH.

The present invention also relates to a process for restoring auxotrophy, preferably uracil auxotrophy to cells of a strain of glycolipid producing micro-organisms previously transformed to prototrophy with a selectable marker, preferably a URA 3 selectable marker, comprising the steps of:

(a) selecting or screening for spontaneous mutations which inactivate the selectable marker and isolate auxotrophic mutants derived from said previously transformed strain, (b) confirming the selectable marker auxotrophy of the mutants, (c) confirming the parental genotype of the auxotrophs by Southern hybridization to appropriate gene probes.

Preferably the process for restoring auxotrophy, preferably uracil auxotrophy to cells of a strain of glycolipid producing micro-organisms previously transformed to prototrophy with a selectable marker, preferably a URA 3 selectable marker, comprises the steps of:

(a) transforming prototrophic host cells with a non-functional selectable marker gene which has been made non-functional by an in-vitro deletion of a portion of the central coding sequence of the gene to produce auxotrophic mutants, (b) confirming the selectable marker auxotrophy of the mutants, (c) confirming the parental geneotype of the auxotrophs.

Yet another aspect of the present invention relates to a process for blocking the beta-oxidation pathway in a glycolipid producing host strain.

This process comprises the steps of disrupting in the host through homologous recombination at least one gene encoding for enoyl-CoA hydratase and 3-hydroxyacyl-CoA dehydrogenase. A preferred embodiment of this process comprises the step of disrupting through homologous recombination at least the MFE2 gene or at least one combination thereof with a linear DNA fragment comprised of a selectable marker gene. Herein, the selectable marker gene is preferably flanked on both ends by at least one DNA sequence having homology to the target genes of the host strain, preferably a *C. bombicola* host strain. Preferably, the selectable marker gene is a URA3A marker gene.

A further aspect of the invention relates to a cell of a glycolipid producing micro-organism strain, having a chromosomal gene which has been disrupted through homologous recombination with a linear DNA fragment comprised of a selectable marker gene which is flanked on both ends by DNA sequences having homology to the chromosomal gene of the corresponding host strain. Herein, preferably the chromosomal gene is a chromosomal MFE2 gene. Herein preferably the selectable marker gene is a URA3A marker gene. The preferred micro-organism is *Candida bombicola*.

The invention further relates to a method for producing glycolipids, using the mutated micro-organism obtained with the process as described above or using the micro-organism as described above.

The process for producing glycolipids of this invention comprises of the following steps:

1. culturing a mutant strain of a microorganism producing glycolipids obtained by mutagenesis as described above, in a medium consisting essentially of an energetic substrate including at least one carbon source and 2. subjecting said strain to a bioconversion substrate, which contains at least one primary or secondary alcohol or diol, at least one fatty acid or fatty acid ester, in which the hydrocarbon chain which determines the chain length contains about 4 to about 24 carbon atoms or a mixture of two or more of those.

A preferred embodiment of this invention relates to a method for producing sophorolipids with medium length hydrocarbon chains, i.e. hydrocarbons having 6-14 carbon atoms in the length determining chain.

Within the scope of this invention glycolipid is understood to comprise those surfactants that have been obtained through microbial cultivation and consist of carbohydrates bound to aliphatic acids or aliphatic hydroxyl acids through glycosidation or acylation. The glycolipid, may be any glycolipid known to the person skilled in the art, in particular it may be a rhamnolipid, sophorolipid, cellobioselipid, trehaloselipid, mannosyl erythritol lipid and (bio)chemical modifications thereof. The person skilled in the art will be capable of selecting the appropriate micro-organism taking into account the nature of the envisaged glycolipid.

Preferably, the glycolipid is a sophorolipid corresponding to the formula:

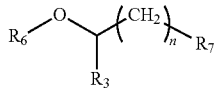

wherein
$R_3 = -(CH_2)_m H$
$R_4 = -(CH_2)_p H$
In which $(m+n+p) \geq 2$ and $\leq 22$ and m, n, and p are independent of one another and $\geq 0$ and $\leq 22$,
$R_7 = -COON$ or $-C(R_4)(R_5)H$
$R_5 = -H, -OH$ or $R_6$

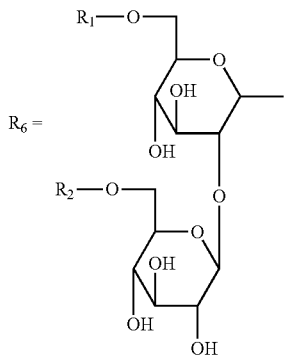

$R_1$ and $R_2$ are independent of one another and —H or —C(O)CH$_3$.

The process of this invention for producing glycolipids, in particular sophorolipids described above preferably comprises culturing *C. bombicola* mutant strain M18, M30 or M33 obtained according to claims 1-10 in a culture medium containing a nitrogen source, an organic substrate and a co-substrate, the M30 strain being most preferred.

The pH of the culture medium after maximum cell density is reached is preferably maintained between 2 and 7, preferably between 3 and 5, more preferably about 3.5.

It is preferred to add the substrate continuously to the culture medium, more preferably at a rate of between 0.1 and 1 gram per litre per hour. The residual concentration of the substrate in the culture medium is preferably kept below 10 g/l, preferably 8 g/l, more preferably 2 g/l.

As a co-substrate preferably use is made of glucose at an initial concentration of at least 100 gram glucose per litre, preferably at least 120 g/l, and in that an excess glucose concentration is maintained above an excess of about 20 g/l. Thereto, glucose may be added in a discontinuous or continuous manner. The oxygen partial pressure of the culture solution is preferably kept $\leq 40\%$ of the saturation value, preferably $\leq 15\%$ of the saturation value. The culture medium may contain a nitrogen source, however in that case the concentration corresponds to 0.5-5 g/l of ammonium chloride, preferably about 1.5 g/l ammonium chloride.

Optimum yield is achieved with a culture medium containing between 0.5 and 25 g/l of yeast extract, preferably between 1 and 15, more preferably between 1 and 10, most preferably about 4 g/l yeast extract.

Within the scope of the present invention, all substrates considered suitable by the person skilled in the art may be used. Suitable examples include compounds responding to the formula $$R^{10}-R^1-X-Y-Z-R^2-R^{20} \qquad \text{(formula I)}$$

which contains at least one cleavable bond,
wherein
—Y is —O—, —S—, —NH—, a mono or di unsaturated bond
X and Z may be the same or different and are chosen from the group of a —CO— group or a —CH$_n$(CH$_2$)$_m$— group which may be straight or branched, with m having a value between 0 and 4 and n between 0 and 2
$R^1$ and $R^2$ each are aliphatic hydrocarbon chains which may be the same or different chain, which may be branched or unbranched, may contain one of more unsaturated bonds and may contain one or more substituents
—$R^{10}$ and $R^{20}$ may be the same or different and are chosen from the group of —H, —CH$_3$, —CHO, —CH$_2$OH, —COOH, —CHS, —CH$_2$SH, —CN or —CH$_2$NR$^3_p$, R$^3$ being an aliphatic hydrocarbon chain or H, p being 1 or 2
or a salt or a methyl, ethyl or glycerol ester thereof.

The preferred substrate however is a primary or secondary alcohol or diol having from about 4 to about 24 carbon atoms, preferably from about 8 to about 14 carbon atoms, primary alcohols being particularly preferred. Preferred primary alcohols include 1-dodecanol or 1-tetradecanol.

For the production of medium chained sophorolipids at high yield and selectivity, preferably use is made of a *C. bombicola* strain M30 which has been cultured in a culture medium containing a nitrogen source, an organic substrate and a co-substrate, the substrate being selected from primary or secondary alcohols or diols, preferably a primary alcohol.

The invention is further elucidated in the example given below.

Example 1

Strains, Plasmids and Culture Conditions—DNA Isolation and Sequencing

*C. bombicola* ATCC 22214 was used for the preparation of genomic DNA. *Escherichia coli* DH5α was used in all cloning experiments. *C. bombicola* was maintained on agar plates containing 10% glucose, 1% yeast extract and 0.1% urea. Yeast strains presumed to lack β-oxidation activity were tested for growth on Yeast Nitrogen base with Oleic acid (YNO) plates (0.67% yeast nitrogen base without amino acids, 0.02% Tween 40 and 0.1% oleic acid). Sophorolipid synthesis of yeast strains with a blocked β-oxidation activity was tested on medium as described by Lang et al. (2000) with either 1-dodecanol (Sigma) used as hydrophobic carbon source in a concentration of 20 or 5 g/L or rapeseed oil (Sigma) used at 37.5 g/L. The hydrophobic carbon source was MFE-2 Sequence.

The nucleotide sequence of the MFE-2 gene of *C. bombicola* has been deposited at the GenBank nucleotide database under the accession number EU315245 and is given in enclosure 1.

TABLE 2

| SEQ ID NO | Name | Feature | Sequence |
|---|---|---|---|
| SEQ ID NO 4 | MFE2_3545For | cloning MFE2 | 5'-CTCCTAAGCATTTAACTGCCTTGAG-3' |
| SEQ ID NO 5 | MFE2_3545Rev | cloning MFE2 | 5'-AACCGAGATACGCCTAATCAGTC-3' |
| SEQ ID NO 6 | URA3infMFE2For | ligating Ura3 into MFE2 | 5'-TGCGTTGCCCCTACACTGACGGGCGGATAGTACA-3' |
| SEQ ID NO 7 | URA3infMFE2Rev | ligating Ura3 into MFE2 | 5'-TGGTCTTCGCCCTCACATCATCGTCACTATACAC-3' |
| SEQ ID NO 8 | MFE2knock1000For | 4095 bp knock-out fragment | 5'-GGCAACTTTGGCCAGGCCAATTA-3' |
| SEQ ID NO 9 | MFE2knock1000Rev | 4095 by knock-out fragment | 5'-GTTTAGATGTGGCTCAAGTA-3' |
| SEQ ID NO 10 | MFE2knock500For | 3070 by knock-out fragment | 5'-TACTGGTGCGGGAGGCGGAATTG-3' |
| SEQ ID NO 11 | MFE2knock500Rev | 3070 by knock-out fragment | 5'-GGTGGCTTGTTGGCTGCTGTGAT-3' | added two days after inoculation and the cultures were incubated for another eight days, unless specified otherwise.

Liquid yeast cultures were incubated at 30° C. and 200 rpm. *E. coli* was grown in Luria Bertani (LB) medium (1% trypton, 0.5% yeast extract and 0.5% sodium chloride) supplemented with 100 mg/l ampicillin and 40 mg/l X-gal if necessary. Liquid *E. coli* cultures were incubated at 37° C. and 200 rpm.

All PCR products were cloned into the pGEM-T® vector (Promega).

Yeast genomic DNA was isolated with the GenElute™ Bacterial Genomic DNA Kit (Sigma). Cell lysis was performed by incubation at 30° C. during 90 minutes with zymolyase (Sigma). Plasmid DNA was isolated with the QIAprep Spin Miniprep Kit (Qiagen). All DNA sequences were determined at the VIB Genetic Service Facility (Belgium).

Example 2

Transformation

*C. bombicola* cells were transformed with the lithium acetate method (Gietz and Schiestl, 1995), but 50 mM LiAc was used instead of 100. Transformants were selected on synthetic dextrose (SD) plates (0.67% yeast nitrogen base without amino acids (DIFCO) and 2% glucose). *E. coli* cells were transformed as described by Sambrook and Russell (2001).

Creation of the Knock-Out Fragments

Figure 5:
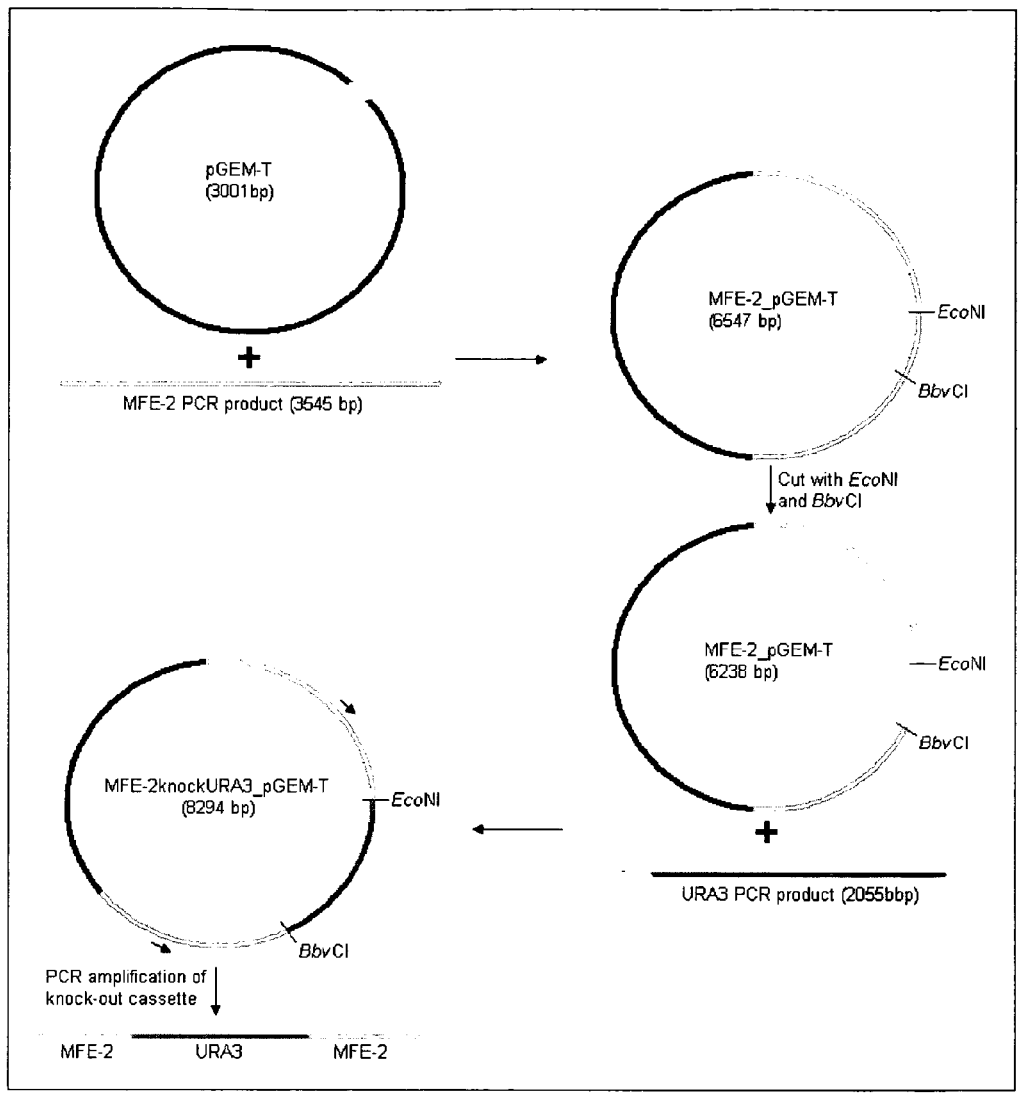
FIG. 5: Creation of the MFE-2 knock-out cassette with the URA3 selection marker for use in *C. Bombicola*.

The 2655 bp coding fragment and 493 and 397 bp upstream and downstream of the MFE-2 gene were amplified with the primers MFE2_3545For and MFE2_3545Rev, yielding a fragment of 3545 bp which was cloned into the pGEM-T® vector (Promega). The created vector was digested with EcoNI and BbvCI, which both cut the coding sequence of MFE-2 once, thus deleting 309 bp of the MFE-2 sequence. The URA3 gene of *C. bombicola* was inserted by means of the In-Fusion™ 2.0 Dry-Down PCR Cloning Kit (Clontech). The primers URA3infMFE2For and URA3infMFE2Rev were designed according to the guidelines of the manual and used for integration of the functional *C. bombicola* URA3 sequence (2055 bp) into MFE-2. The primerpair MFE2knock1000For and MFE2knock1000Rev were used for the amplification of a 4095 bp fragment containing the URA3 sequence with approximately 1000 bp of the MFE-2 sequence on each site. In the same way the primers MFE2knock500For and MFE2knock500Rev were used to create a construct of 3070 bp with 500 bp flanking regions. Finally, a larger fragment (5287 bp) with 1962 bp and 1272 bp flanking respectively the 5' and 3' site of the URA3 sequence was created with the MFE2_3545For and MFE2_3545Rev primerpair. The creation of the knock-out cassettes is illustrated in FIG. 5.

Cell Dry Weight.

Cell dry weight was measured by centrifugation of 2 mL culture broth for 5 min at 9 000 g. Pellets were washed two times with ethanol to remove sophorolipids and lipophilic substrate and finally dissolved in distilled water. The suspension was transferred to a cellulose nitrate filter with a pore diameter of 0.45 μm (Sartorius) and the dry weight was determined in the XM60 automatic oven from Precisa Instruments Ltd.

Sophorolipid Production.

Analytical sophorolipid samples were prepared as follows: 440 μL ethyl acetate and 11 μL acetic acid were added to 1 mL culture broth and shaken vigorously for 5 min. After centrifugation at 9 000 g for 5 min, the upper solvent layer was removed and put into a fresh eppendrof tube with 600 μL ethanol. Samples were analysed as described below.

Final Sophorolipid Extraction from Culture Broth.

This protocol is described in Fleurackers (2006).

HPLC-Analysis.

Sophorolipid samples were analysed by High Performance Liquid Chromatography (HPLC) on a Varian Prostar HPLC system using a Chromolith® Performance RP-18e 100-4.6 mm column from Merck KGaA at 30° C. and Evaporative Light Scattering Detection (ELSD, Alltech). A gradient of two eluents, a 0.5% acetic acid aqueous solution and acetonitrile, had to be used to separate the components. The gradient started at 5% acetonitrile and linearly increased till 95% in 40 min. The mixture was kept this way for 10 min and was then brought back to 5% acetonitrile in 5 min. A flow rate of 1 mL/min was applied.

According to the teaching of Brachmann et al, 1998, knocking out genes in *S. cerevisiae* is relatively simple: by means of PCR one can construct a linear fragment containing a marker flanked on each site by only 40 bp of the target gene and transform the yeast cells with this construct. Since *S. cerevisiae* laboratory strains are very efficient in homologues recombination, events of double cross-over or gene replacement occur frequently enough to yield the right transformants. This strategy was also tested for *C. bombicola*; the functional URA3 sequence was flanked with 60 bp of the *C. bombicola* MFE-2 gene and used to transform the ura3-auxotrophic G9 strain described by Van Bogaert et al, (2008). This did however not yield proper transformants. 60 bp homology is probably too short for efficient recombination with the *C. bombicola* genome. Therefore, a disruption vector was created as described in the Materials and Methods. It contains the 2055 bp of the URA3 coding sequence with promoter inserted into the MFE2 sequence. The vector was then used as a template in PCR reactions with the primers listed in Table V-1 to create a linear marker sequence flanked with MFE-2 sequences of a variable length. In this way fragments with about 500, 1000 or more bp of the MFE-2 gene on both ends were created with a total length of respectively 3070, 4095 and 5287 bp. 1.5 μg of each of the three fragments were used to transform *C. bombicola*. The fragment with 1000 bp flanking regions yielded about threefold more transformants compared to the other two.

It was found that when transforming the ura3-auxotrophic G9 *C. bombicola* strain with a functional URA3 gene, double cross-over with a consequent gene replacement takes place at a rate of 19%.

All other transformants arise owing to events of single cross over or illegitimate recombination. For this reason, the MFE2-negative candidates obtained were further tested. The correct phenotype was tested by plating the mutants on medium with oleic acid as the sole carbon source (YNO); mutants with a deficient β-oxidation will not succeed in growing on this medium. 9 transformants were not able to grow on this medium, while the growth on general YPD medium was good: M9, M15, M16, M18, M24, M27, M30, M32 and M33.

The genotype of the obtained mutants was confirmed by a yeast colony PCR targeting the MFE-2 sequence with the primers MFE2_3545For and MFE2_3545Rev (Table 2). Presence of the intact wild type MFE-2 gene should yield a fragment of 3545 bp, whereas for yeasts with the knocked-out MFE-2, this fragment must be either absent or appear as a larger band of about 5000 bp. All 9 strains selected by their non-growth on YNO-plates displayed the right genotype.

Evaluation of Sophorolipid Synthesis by the MFE-2 Negative Strains.

The inventor has observed that by knocking out the β-oxidation, the hydroxylated medium-chain substrates could be re-directed towards sophorolipid biosynthesis.

Figure 2:
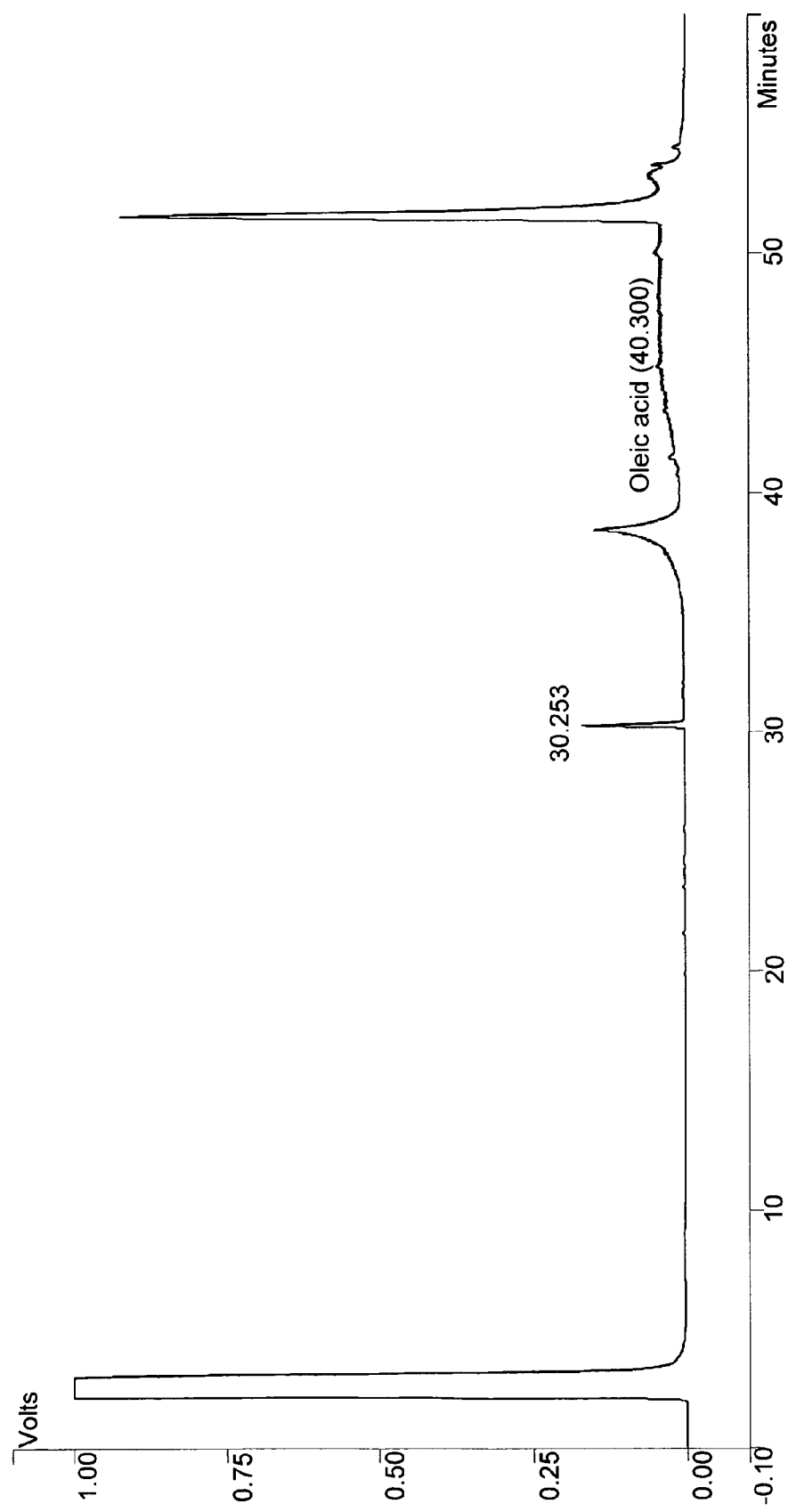
FIG. 2: Sophorolipids from wild type *Candida* grown on 1-dodecanol (medium chain Sophorolipids at 30.2 min, no wild type Sophorolipids at 29.9 min).
Figure 3:
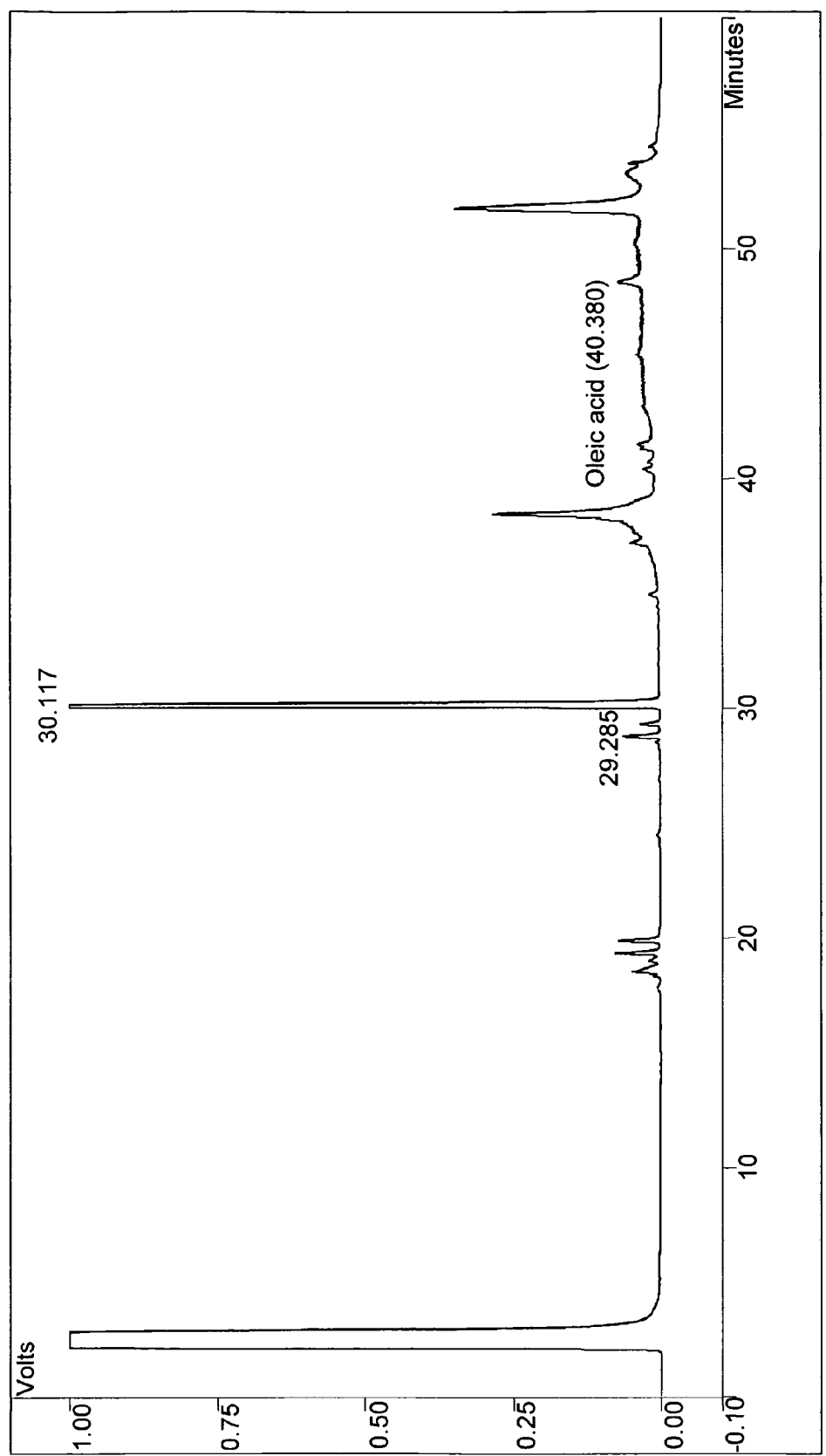
FIG. 3: Sophorolipids from *Candida* mutant strain M18 grown on 1-dodecanol (medium chain Sophorolipids at 30.2 min, wild type Sophorolipids at 29.9 min).
Figure 4:
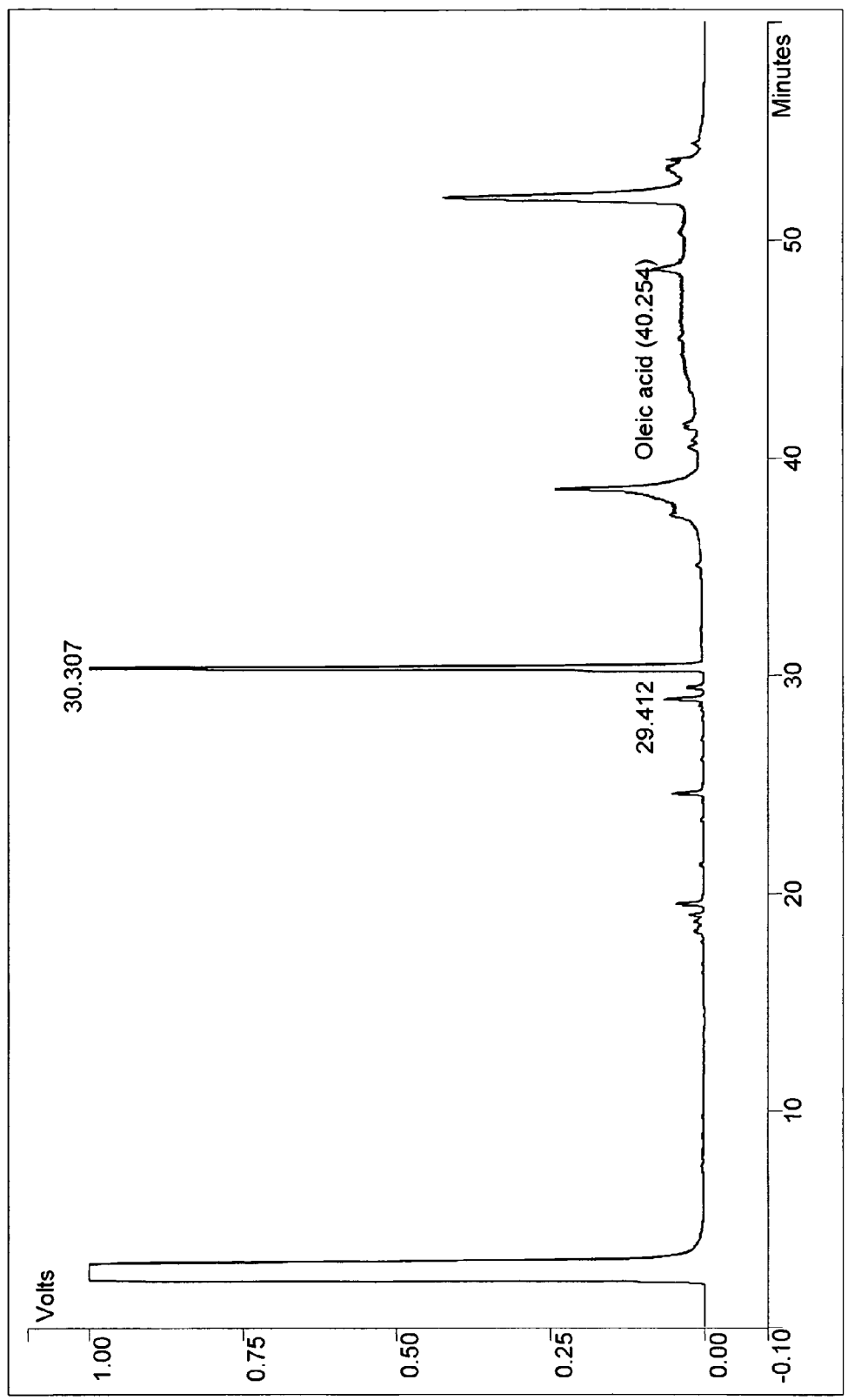
FIG. 4: Sophorolipids from *Candida* mutant strain M33 grown on 1-dodecanol (medium chain Sophorolipids at 30.2 min, wild type Sophorolipids at 29.9 min).

Thereto, use was made of 1-dodecanol as a substrate because of its good solubility at 30° C. which facilitates sophorolipid synthesis and sampling. The results of the fermentations run on 1-dodecanol are illustrated in HPLC chromatograms given in FIG. 1 for the wild type *Candida bombicola* ATCC 22214 grown on rapeseed oil (FIG. 1) and grown on 1-dodecanol (FIG. 2) and for two mutant strains M18 and M30 grown on 1-dodecanol (FIGS. 3 and 4). Wild type sophorolipids from rapeseedoil, which mainly contains monounsaturated C18 sophorolipids, elute at about 29.2 minutes (see FIG. 1) medium C12 chain sophorolipids at about 30.1-30.2 minutes. FIG. 2 shows that the wildtype *Candida* strain hardly produces any of these medium chain sophorolipids, whereas M18 and M30 yield a very pronounced C12 peak and virtually no C18 sophorolipids, so with highly selectively transforming the alcohol substrate to the envisaged medium chain sophorolipids. The medium chain sophorolipid yields are listed in Table 3 for all obtained mutant strains.

TABLE 3

Sophorolipid production on 1-dodecanol of mutant strains relative to the wild type.

| Strains | Relative amount of sophorolipids (%) | CDW (g/L) | CDW corrected relative amount of sophorolipids (%) |
|---|---|---|---|
| Wild type | 100.0 | 7.0 | 100.0 |
| M9 | 285.7 | 9.0 | 222.2 |
| M15 | 262.9 | 9.5 | 193.7 |
| M16 | 237.1 | 9.0 | 184.4 |
| M18 | 274.3 | 8.0 | 240.0 |
| M24 | 217.1 | 7.5 | 202.7 |
| M27 | 254.3 | 9.0 | 197.8 |
| M30 | 308.6 | 7.5 | 288.0 |
| M32 | 262.9 | 11.0 | 167.3 |
| M33 | 278.0 | 8.5 | 228.9 |

A total mass of 9.5 g/L sophorolipids was synthesized by the wild type, while for all mutant strains clearly better results were obtained; the overall yield was 2.2 till 3.1 times higher.

Since biomass formation differs among the strains and is slightly lower for the wild type, this factor was taken into account for correct comparison of the obtained sophorolipid values. Still, sophorolipid production of the mutant strains stayed 1.7 to 2.9 times higher as compared to the wild type; it therefore can be concluded that strains with a blocked β-oxidation route perform better when synthesizing sophorolipids on 1-dodecanol.

To produce dodecyl sophoroside, 100 ml of a culture medium of the following composition was introduced into a 500 ml Erlenmeyer flask with baffles:

Glucose.H$_2$O 150.00 g/l (U.S. Pat. No. 5,767,255 slechts 100 g/l)
Sodium citrate.3H$_2$O 5.00 g/l
Yeast extract (granulated, Merck, Darmstadt) 4.00 g/l
Ammonium chloride 1.54 g/l
Potassium dihydrogen phosphate 1.00 g/l
Magnesium sulfate.7H$_2$O 0.70 g/l
Sodium chloride 0.50 g/l
Calcium chloride.2H$_2$O 0.27 g/l
Dipotassium hydrogen phosphate.3H$_2$O 0.16 g/l The medium was inoculated with the yeast *Candida bombicola* ATCC 22214 and incubated on a rotary shaker at 100 rpm at a temperature of 30° C. After a cultivation time of 48, 72 and 96 h, in each case 5 g/l 1-dodecanol were added under aseptic conditions to the culture solution. The culture was carried out under unchanged conditions between and after the additions of the alcohol. The pH of the culture suspension decreased over the entire range of cultivation. After a cultivation period of 10 days, the supplied amount of alcohol had been converted; the cultivation was then stopped.

To isolate the products, the culture suspension was neutralized with 1N sodium hydroxide solution and then extracted twice with twice the volume of ethyl acetate. The organic phases were separated off, combined and dried over anhydrous sodium sulphate. After removal of the desiccant on a paper filter, the solvent was removed by distillation under reduced pressure in a rotary evaporator.

*Candida bombicola* strains M18, M30 and M33 are the optimum yeast strains used in the present invention to produce medium chained sophorolipids and were deposited at the BCCM/MUCL Culture Collection of the Mycothèque de l'Université Catholique de Louvain, Belgium under the provisions of the Budapest Treaty on May 21, 2008, under accession numbers MUCL 51389, MUCL 51390 and MUCL 51391 respectively. The subject culture deposit will be stored and made available to the public in accord with the provisions of the Budapest Treaty for the Deposit of Micro-organisms.

Comparative Example A

Production of medium chain sophorolipids by the wild-type *Candida* were carried out as described below. All experiments were carried out using 1-dodecanol as the lipophilic substrate and utilised medium according to Lang et al. (Chem. Today, 2000, 18, p. 76-79). One shakeflask experiment and two bioreactor experiments were carried out. The shakeflask experiment used the wild-type *Candida* as a reference and was carried out in twofold. Of the bioreactor experiments, one was done under aerobic conditions and the other employed a limited aeration.

Shakeflask Experiments.

For each shakeflask, a test tube containing 10 ml of medium was inoculated with either the wild-type or the M30 strain and left to grow for two days at 30° C. The test tubes were shaken regularly (approx. 7 times a day) to prevent the cells settling on the bottom. Two 500 ml baffled shakeflasks per strain, each containing 200 ml of medium, were inoculated with the contents of one appropriate test tube and were left to grow for two and a half days at 30° C., shaking at 150 rpm. The first portion of 3.45 g 1-dodecanol per flask was added after this period of growth. The second, equally large portion of substrate was added four days after. Four days later the experiment was stopped. Sampling was performed on the $1^{st}$, $2^{nd}$, $3^{rd}$, $4^{th}$, $7^{th}$ and $8^{th}$ day after the first portion was added. 1 mL of broth was transferred to 3 mL of ethanol, mixed vigorously and filtered over a 0.45 µm membrane to remove the cells. The resulting solution was then analysed by reversed phase HPLC. Chromatograms obtained from the M30 samples of day 8 clearly showed the emergence of new peaks in the area between the fronting peak and the area in which the known $C_{16}/C_{18}$ sophorolipids occur. This area is concurrent with molecules that are more hydrophilic than these known sophorolipids but more hydrophobic than salts and, for example, wetting agents. The theoretically predicted structure of short chained sophorolipids indicates that they are to be found in this region. No peaks were found in this region for samples taken from the wild-type cultures. Identical peaks and peak patterns were found after cultivation in a bioreactor.

Bioreactor Experiments.

For each experiment, two test tubes containing 10 ml of medium were inoculated with the M30 strain and grown as indicated above for the shakeflask experiments. These were used to inoculate 500 ml of medium which was left to grow for two days at 30° C. while magnetically stirring. This inoculum was then added to 3 L of medium and grown for two and a half days. The medium was kept at 30° C. and aerated with 1 v/vm which is 1 volume of air per volume medium and per minute of air while stirring at 300 rpm, no pH correction was made. For the fully aerated experiment, the stirring speed was increased to 550 rpm after the growth phase and kept at this value throughout the entire experiment so the $pO_2$ never dropped below 10% and had an average of 40%. For the experiment with limited aeration, the airflow and stirring speed were adjusted after the growth phase in order to keep the $pO_2$ between 1% and 10%. In both experiments, the pH remained between 3 and 4. Six days after the experiments were started, an additional 175 g of glucose was added. In each case, the substrate was added step-wise during the first four days after completion of the growth phase. In the fully aerated experiment, 175.8 g of 1-dodecanol was added; the experiment with limited aeration received a total of 156.5 g 1-dodecanol.

Sampling throughout both experiments was done in a similar fashion as for the shakeflask experiments, except that samples of 3 ml of broth were added to 9 ml of ethanol. Additionally for the experiment with limited aeration, the total dry biomass after the growth phase was determined several times on 12 ml of broth and was found to be stable around 10 g/L. The total duration, from inoculation of the bioreactor to final sampling, of both experiments was ten days.

The final broth of the fully aerated experiment exhibited a top layer of insoluble solids and consisted mostly of dodecanoic acid. As samples taken from the aqueous phase did not contain any appreciable amounts of hydrophobic (i.e. more hydrophobic than $C_{16}$-$C_{18}$ sophorolipids) compounds, it is assumed that any 1-dodecanol which was not converted into sophorolipids was in fact oxidised to dodecanoic acid.

Analysis of the Reaction Product Using Chromatography.

Analysis of the samples was done similarly as for the shakeflask samples. The resulting chromatograms where divided into four areas as to correlate retention time to a certain functional class (see table 4). The total peak surface of each area was calculated. As the detection method used returns a quadratic response, the square root of each of the four totaled surface areas was calculated and these values were used to determine the percentage in which components of each functional class were present. The analysis of 100 ml of broth from the experiment with limited aeration yielded 27.4 g/L of non-volatile water soluble components (out of 83.3 g/L dry matter, biomass excluded) out of which 30% was found in the $2^{nd}$ area; it is therefore concluded that 8.2 g/L of medium-chained sophorolipids were formed. The direct comparison of the chromatograms from equal amounts of either fully or limited aerated broth indicate a that the root of total area 2 is approximately 3.4 times larger in the case of limited compared to full aeration. As such it is concluded that using limited aeration increases production more than three-fold.

Analysis of the Reaction Product Using Mass Spectrometry.

Mass spectrometry analysis of the bioreactor experiment extract showed concurrent masses as expected from the direct conversion of dodecanol into sophorolipids. A relatively small amount of de novo sophorolipids were found as well. An overview of the molecular masses that were found, their assigned structure and their origin is given in table 5.

TABLE 4

Table 1.
Division of chromatogram retention times into functional classes

| Area N° | Retention time @ start (min) | Retention time @ end (min) | Description of the functional class |
|---|---|---|---|
| 1 | 0 | 6 | Salts & components having a HLB higher than surfactants (i.e. hydrotropes) |
| 2 | 6 | 22 | Surfactants with a high HLB value |
| 3 | 22 | 34 | Surfactants with a low HLB value |
| 4 | 34 | 51 | Lipophilic components |

TABLE 5

Molecular masses found in the extract of a bioreactor experiment using dodecanol

| MW (Da) | Assignation | Structure | Origin |
|---|---|---|---|
| 222 | Diethyl phthalate | 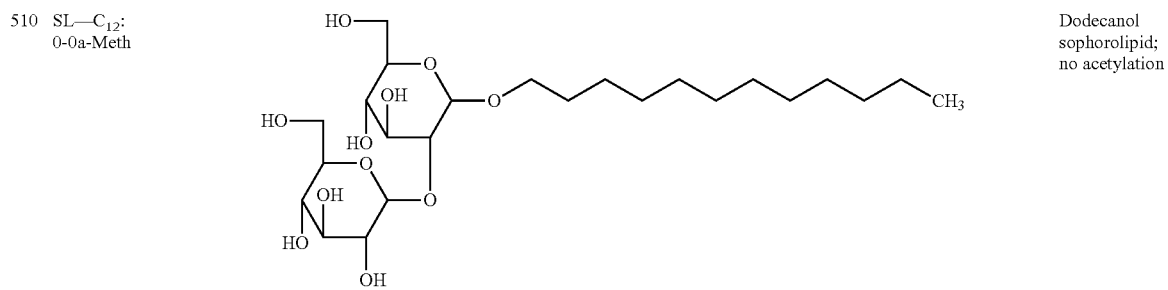 | Agent used for the denaturation of ethanol |
| 510 | SL—C$_{12}$: 0-0a-Meth | 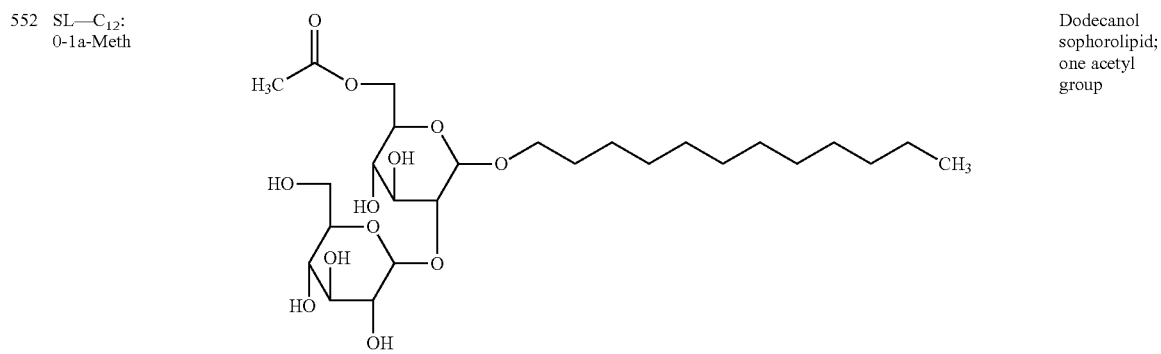 | Dodecanol sophorolipid; no acetylation |
| 552 | SL—C$_{12}$: 0-1a-Meth | 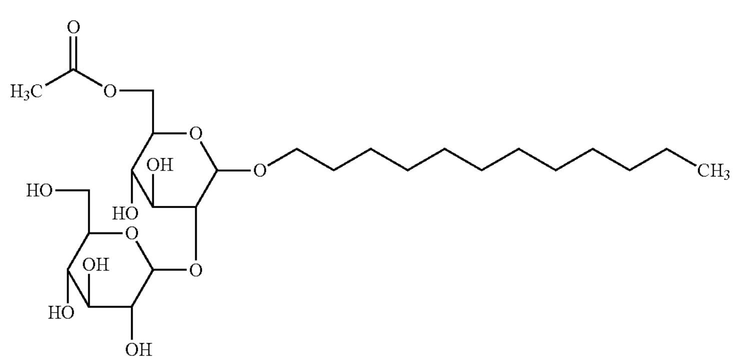 | Dodecanol sophorolipid; one acetyl group |

TABLE 5-continued

Molecular masses found in the extract of a bioreactor experiment using dodecanol

| MW (Da) | Assignation | Structure | Origin |
|---|---|---|---|
| 594 | SL—$C_{12}$: 0-2a-Meth | 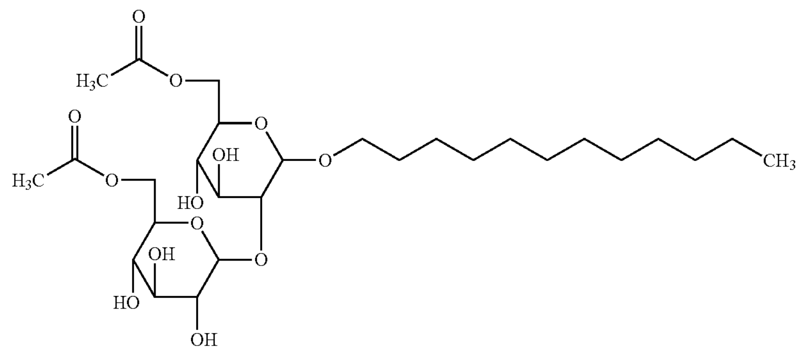 | Dodecanol sophorolipid; two acetyl groups |
| 706 | SL—$C_{18}$: 1-2a-Carb | 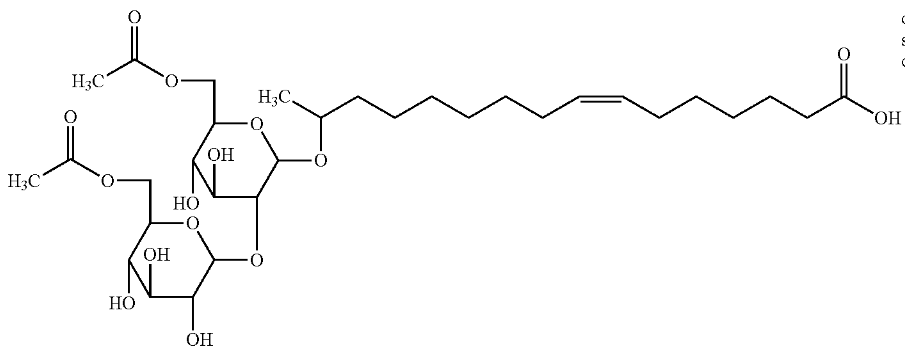 | de novo sophorolipid; open form |

Evidence for said masses was obtained through both positive and negative electrospray ionisation, except for diethyl phthalate, which was only found when using the positive mode. The retention times of the dodecanol-based sophorolipids confirmed that they are to be found in the part of the chromatogram as indicated in table 4.

Analysis of the Reaction Product Using HPLC.

The analytical method used is described in Fleurackers (2003). The gradient used for the analysis was as follows: 0.5% acetic acid to 100% acetonitrile over a time of 40 minutes, 5 minutes of 100% acetonitrile, 1 minute to go to 100% water and 5 minutes of 100% water, always using a flow of 1 ml/min. Ultra pure water was produced in a Synergy 185 ultra pure water system (Millipore) and used in all of the experiments. Additionally the water was kept for approximately 2 hours at 20 mbar to remove any dissolved air. Acetonitrile was Chromesolv® grade (Riedel-de Haën) 100 μl sample was injected twice for analysis. The column was a Chromolith™ Performance RP-18e (Merck; C18; Ø 4.6 mm; length 100 mm), which was protected with a C8 guard column (Supelco Pelliguard™ LC-8, 2 cm). A P580 pump (Dionex) and ASI-100 autosampler (Dionex) were coupled to a PL-ELS1000 (Polymer Laboratories) evaporative light scattering detector. Pump and autosampler were controlled by the Chromeleon™ software version 6.40 (Dionex) and the detector by the PL-ELS1000 control software ver4.0 (Polymer Laboratories). For the detector, nitrogen gas was used at a flow of 1 l/min. Nebulizer temperature was set at 85° C. and evaporator temperature at 90° C. HPLC-data processing was also done using the Chromeleon™ software. The peaks were identified by Intertek using RP-HPLC-MS (Waters ZQ) with electrospray ionisation and quadrupole detection.

From the above given results it appears that no medium chained sophorolipids were synthesized when using the wild-type strain and the use of limiting aeration showed more than a threefold production increase of these sophorolipids when compared to working under fully aerated conditions.

REFERENCES

Van Bogaert I N A, De Maeseneire S L, De Schamphelaire W, Develter D, Soetaert W, Vandamme E J, 2007 Cloning, characterisation and functionality of the orotidine-5'-phosphate decarboxylase gene (URA3) in *Candida bombicola*. Yeast 24, 201-208.

Van Bogaert I N A, De Maeseneire S L, Develter D, Soetaert W, Vandamme E J, 2008. Development of a transformation and selection system for the glycolipid producing yeast *Candida bombicola*. Yeast 25, 273-278

U.S. Pat. No. 5,254,466 Picataggio S, Deanda K, Eirich L D, 1993. Site-specific modification of the candida tropicals genome.

WO9924448 Lang S, Brakemeier A, Wullbrandt D, Seiffert-Stoeriko A, 1999. New sophoroselipids, method for their production and use U.S. Pat. No. 5,767,255 Wullbrandt D, Giani C, Brakemeier A, Lang S, Wagner S, 1998. Glucose- and sophorose-lipids, a process for their preparation and their use Sambrook J. and Russell D. W. 2001. Molecular Cloning: *A Laboratory Manual*. $3^{rd}$ ed. Cold Spring Harbour Laboratory Press, Cold Spring Harbour, New York.

Gietz, R. D. and R. H. Schiestl. 1995. Transforming yeast with DNA. *Methods Mol. Cell. Biol.* 5: 255-269.

Fleurackers S J J. 2006. On the use of waste frying oil in the synthesis of sophorolipids. Eur J Lipid Sci Technol 108, 5-12.

Fleurackers S., 2003. HPLC analysis of sugar detergents of commercial and ecological interest. La Rivista Italiana delle Sostanze Grasse (Vol. 80, July-August).

The invention claimed is:

1. A process for producing sophorolipids comprising the steps of:
   (1) culturing a mutant strain of a sophorolipids producing *Candida bombicola* comprising disruption of the MFE2 gene, in a medium comprising an energetic substrate including at least one carbon source; and
   (2) contacting said strain with a bioconversion substrate, which contains at least one primary or secondary alcohol or diol, or at least one fatty acid or fatty acid ester, in which the hydrocarbon chain which determines the chain length contains about 4 to about 24 carbon atoms.

2. A process as claimed in claim 1, wherein the sophorolipid corresponds to the formula:

$$R_6\text{—O—}\underset{R_3}{\underset{|}{CH}}\text{—}(CH_2)_n\text{—}R_7$$

wherein
$R_3$=—$(CH_2)_m$H
$R_4$=—$(CH_2)_p$H
in which $(m+n+p) \geq 2$ and $\leq 22$ and m, n and p are independent of one another and $\geq 0$ and $\leq 22$,
$R_7$=—COOH or —$C(R_4)(R_5)$H $R_5$ = —H, —OH or —$OR_6$ $R_6$ = [sophorose structure with $R_1$—O and $R_2$—O substituents]

$R_1$ and $R_2$ are independent of one another and —H or —C(O)CH$_3$.

3. A process as claimed in claim 1, comprising culturing *C. bombicola* mutant strain M18, M30 or M33 in a culture medium containing a nitrogen source, an organic substrate and a co-substrate.

4. The process of claim 3, wherein the mutant strain is M30.

5. The process of claim 1, wherein the pH of the culture medium after maximum cell density is reached is maintained between 3 and 5.

6. The process of claim 1, wherein the bioconversion substrate is continuously added to said culture medium at a rate of between 0.1 and 1 gram per liter per hour.

7. The process of claim 1, wherein a residual concentration of the bioconversion substrate in the culture medium is kept below 10 g/l.

8. The process of claim 1, wherein the energetic substrate is glucose at an initial concentration of at least 100 gram glucose per liter, and the excess of glucose concentration is maintained above an excess of about 20 g/l.

9. The process of claim 1, wherein an oxygen partial pressure of the culture solution is ≦40% of the saturation value.

10. The process of claim 1, wherein the culture medium contains a nitrogen source at a concentration which corresponds to 1.5 g/l ammonium chloride.

11. The process of claim 1, wherein the culture medium contains about 4 g/l yeast extract.

12. The process of claim 1, wherein the bioconversion substrate is an aliphatic linear or branched hydrocarbon, which may contain one or more substituents selected from the group consisting of OR, COOH, and an ester with a carbon chain length of about 4 to about 24.

13. The process of claim 12, wherein said bioconversion substrate is a primary or secondary alcohol or diol having from about 4 to about 24 carbon atoms.

14. The process of claim 1, wherein the bioconversion substrate is a primary alcohol.

15. The process of claim 1, wherein the bioconversion substrate is 1-dodecanol or 1-tetradecanol.

16. The process of claim 5, wherein the pH of the culture medium after maximum cell density is reached is maintained at about 3.5.

17. The process of claim 7, wherein the residual concentration of the bioconversion substrate in the culture medium is kept below 8 g/l.

18. The process of claim 7, wherein the residual concentration of the bioconversion substrate in the culture medium is kept below 2 g/l.

19. The process of claim 8, wherein the energetic substrate is glucose at an initial concentration of at least 120 g/l, and the excess of glucose concentration is maintained above an excess of about 20 g/l.

20. The process of claim 9, wherein an oxygen partial pressure of the culture solution is <15% of the saturation value.

21. The process of claim 13, wherein said bioconversion substrate is a primary or secondary alcohol or diol having from about 8 to about 14 carbon atoms.

* * * * *

UNITED STATES PATENT AND TRADEMARK OFFICE
CERTIFICATE OF CORRECTION

PATENT NO. : 8,530,206 B2  
APPLICATION NO. : 12/994077  
DATED : September 10, 2013  
INVENTOR(S) : Develter et al.

Page 1 of 1

It is certified that error appears in the above-identified patent and that said Letters Patent is hereby corrected as shown below:

On the Title Page (item 73, Assignee) at line 2, Change "Antwerp" to --Antwerpen--.

On the Title Page, in column 2 (item 56, under Other Publications) at line 22, Change "offlipids," to --off lipids,--.

In the Specification

In column 1 at line 53 (approx.), Change "and or" to --and/or--.

In column 6 at line 32, Change "geneotype" to --genotype--.

In column 7 at line 36 (approx.), Change "-COON" to -- -COOH--.

In column 9 at line 41, Change "trypton," to --tryptone,--.

In column 10 at line 1 (Table 2), Below "TABLE 2" insert --Primers used for cloning and knocking-out the C. bombicola MFE-2 gene. All primers were obtained from Sigma Genosys.--.

In column 10 at line 16 (approx., Table 2), Change "by" to --bp--.

In column 10 at line 19 (approx., Table 2), Change "by" to --bp--.

In column 10 at line 22 (approx., Table 2), Change "by" to --bp--.

In column 11 at line 9, Change "eppendrof" to --eppendorf--.

In column 12 at line 18 (approx.), Change "rapeseedoil," to --rapeseed oil,--.

In column 12 at line 21 (approx.), Change "wildtype" to --wild type--.

In column 17 at line 52, Change "Chromesolv®" to --Chromasolv®--.

In the Claims

In column 40 at line 15, In Claim 20, Change "<15%" to --≤15%--.

Signed and Sealed this  
Twenty-second Day of April, 2014

Michelle K. Lee  
*Deputy Director of the United States Patent and Trademark Office*

SEQUENCE LISTING

<160> NUMBER OF SEQ ID NOS: 11

<210> SEQ ID NO 1
<211> LENGTH: 6033
<212> TYPE: DNA
<213> ORGANISM: Candida bombicola
<220> FEATURE:
<221> NAME/KEY: gene
<222> LOCATION: (1)..(6033)
<223> OTHER INFORMATION: MFE2 gene
<220> FEATURE:
<221> NAME/KEY: CDS
<222> LOCATION: (1821)..(2423)
<223> OTHER INFORMATION: Coding seqence for putative v-ATPase VO c''
    subunit
<220> FEATURE:
<221> NAME/KEY: CDS
<222> LOCATION: (2910)..(5564)
<223> OTHER INFORMATION: Coding sequence for MFE2

<400> SEQUENCE: 1

```
aaagtcttga gtaggaacgc cccaggagga tgcattgttt ggatgaaacc cgctcgaatc    60
tgccgagttt tctttcccga ttcgagaagg attttgagga aacggcatac gacaataagg   120
atacccaaat gggacgactg aaccgtttgt gtaggggat aagggagcgt tctgtgttgc    180
catgtactgc agatttgcca taggattata tattggcatt gttcctgtga cataatttga   240
agctgaagat cggtactccg gaggcacaaa gttcctgggc tggtagatat gagttggaag   300
cataggaagg ggtagcatga agttggctgg ctgatccagc tccatcgcgt caagccggct   360
ttccgggatt ctagcgtaag cggcttgagt cggtgatgtg tcgactcctt gatatcggat   420
tgtatcttca tctggtaccg cgcaaagcga tggtggtttg tagttcgcta gtcccgacgt   480
gactaaattc cggtaagagg tttctccaac gccggaggac aatagcttcc gctgcgtggc   540
ctccgcttgt gatttcatgt tttccaggat tgaactcatt ggcacctctg ccatttctgt   600
attgtcagtg tcaacatctc cgctgagttc ctcctcactc tcattagacc tgatacaaac   660
ttcttgcttg catgattcag tgggattctg gaaagaaagc tcctctctta ctgatatgaa   720
agagtcctca ttccaatatc tcccattctg gtggtctgct cgttttttggc ctctcatttc   780 ctctaaaatt agagctgcgg aagctttcgt tccctgaatg ttatccaaat tcaaagtgtt   840
gactgtcagc gcttgcttcg atctacttcc aacagaataa ggtctatcgg acgcatcact   900
ctcaactgaa tgtgccaatg tcggagttgg aaagttatgc cttcctttgc tatagtcccc   960
aatttgatcc aagcgcgaag gggaatctag agcgtctatg agtatcgtgt tcttttcgtt  1020
taactctggc aaacaagcta cgtccgcggc agatttcatc cccggggacg gtatcaagaa  1080
tgtgatgttc gtaaccaatt gatggggcaa aagccaagtg ctacgctaga ttgccttaaa  1140
ctttaacgcc acctctgata agtggccaaa atctctggtt aagtcatttg acaaatttag  1200
tgtacattct agctttcgca tagattgcat acaccctagc ccacatatgc aagttctcgc  1260
attaacctca ggttcctact gcgtgcctga gtcttgcaag ttgaagctcg actgcatgat  1320
tatgcgagcc aacaacaaaa gcctcgactg aggggtcact tatcaaaaaa attactggct  1380
gagcaattat ggaagtttgg ttgaccaaca agttactaac ttcagcgctt ttcactcaac  1440
tccccatggg caagttacaa ggacattaag cttttctgca ggtctaatca atgtcaagtg  1500
```

```
gaacgttaaa gacaatcgca cagaatgatg gcatcgaatt ccgtgtttct caaaatagtg    1560
gagggttttt tcgtgccctg cttttagcca tagccagacg gattcgatct catatcgagc    1620
aggattactg gaaattgtgc cctccaatcc gacccaagaa tgcttgaaga gttgtgatta    1680
tgtggttagt ttttttggcag cggcgtgaca cgtgacgtat agtcagcaat ctctgtgcca   1740
gcatttggga tcaacgcagc caagaagccc agttccgtca attggagctg tcaaactgaa    1800
ggtatattga cccagaatat atg ggc gcg ctg gcc tac agt ttg ttg ggg ctc   1853
                       Met Gly Ala Leu Ala Tyr Ser Leu Leu Gly Leu
                        1               5                  10 tct gcc ctg gca gca gtt gta gca gga tct tac gct ctc ttc aca gga     1901
Ser Ala Leu Ala Ala Val Val Ala Gly Ser Tyr Ala Leu Phe Thr Gly
         15                  20                  25 cag ggc tcc cag ttt gat gtt ggt cat ttc cta ttg acg acc agt ccc     1949
Gln Gly Ser Gln Phe Asp Val Gly His Phe Leu Leu Thr Thr Ser Pro
         30                  35                  40 ttc atg tgg gct ctt ctg gga gtt ccc ctt tgc aca ggg cta agc ata     1997
Phe Met Trp Ala Leu Leu Gly Val Pro Leu Cys Thr Gly Leu Ser Ile
     45                  50                  55 gct ggt gcc gct tgg gga att ttc ata act gga acc agt att ctc ggg     2045
Ala Gly Ala Ala Trp Gly Ile Phe Ile Thr Gly Thr Ser Ile Leu Gly
 60                  65                  70                  75 gcg agt gtc aaa gtg cca aga gtt act aca aag aac ctt gtg tct gtt     2093
Ala Ser Val Lys Val Pro Arg Val Thr Thr Lys Asn Leu Val Ser Val
                 80                  85                  90 gtg ttt tgt gaa gtg gtg gct att ttt ggg cta atc acg tca att gtg     2141
Val Phe Cys Glu Val Val Ala Ile Phe Gly Leu Ile Thr Ser Ile Val
             95                 100                 105 ctt tct tcg aag atc tca tca act ggt ttc aac aca gca ctc tcg aag     2189
Leu Ser Ser Lys Ile Ser Ser Thr Gly Phe Asn Thr Ala Leu Ser Lys
        110                 115                 120 gaa aac tta ttc act gga tat gct gtg ttt tgg gct ggc ctg act gtc     2237
Glu Asn Leu Phe Thr Gly Tyr Ala Val Phe Trp Ala Gly Leu Thr Val
    125                 130                 135 ggt gtg tct aac ttg gtt tgt ggt gtc kct gtg gga gtt gct ggc gcc     2285
Gly Val Ser Asn Leu Val Cys Gly Val Xaa Val Gly Val Ala Gly Ala
140                 145                 150                 155 act gct gca gtt tct gat gct gca gat cct agt tta ttc gtc aaa att    2333
Thr Ala Ala Val Ser Asp Ala Ala Asp Pro Ser Leu Phe Val Lys Ile
                160                 165                 170 ctc gtc atc gag atc ttt ggg tct gtg att ggc cta ttt ggg cta atc    2381
Leu Val Ile Glu Ile Phe Gly Ser Val Ile Gly Leu Phe Gly Leu Ile
            175                 180                 185 gtt gga ttg ctc atg tcc act gaa gcc cct gaa ttc tcc taa            2423
Val Gly Leu Leu Met Ser Thr Glu Ala Pro Glu Phe Ser
        190                 195                 200 gcatttaact gccttgagaa acaatattta caccgaaaaa cgttcggagc tcgtatgtac   2483
tcaatagcgc caaccatttt ttatgtacct gccaggtcgc attaaaactt gcatgttgtg   2543
actgtacgag ctcaaagcga tgacttagac ccatagatat tcatacaatt ataggtatct   2603
gaataaagcg ccttgccaaa tgaatctcat ttgaacaatt atgcgaattg agagcgctag   2663
accataaaaa agcaggcgat ttaatttcgc caatgccgag gctgcatggt ggagatatgt   2723
ctgaatttcg gcggataggt acccttacct caacccaaaa gtgcgggggg aagcccgact   2783
gtctgccgat actttatggc gcagttccgc aatagccgag tggggtcgtg catatatata   2843 tagggggtcac tcatcattcg attgtgagat aaactacatt gaaaatacaa gaagggaaag  2903 tgaaac atg gcg gag aat ctt agg tac gac ggc aaa gtt gtc gtt gtc     2951
       Met Ala Glu Asn Leu Arg Tyr Asp Gly Lys Val Val Val Val
```

|  |  | 205 |  |  |  |  | 210 |  |  |  |  |  |  |  |
|---|---|---|---|---|---|---|---|---|---|---|---|---|---|---|
| act | ggc | gca | gga | ggc | gga | ctt | gga | aaa | gcc | tac | gcg | ctg | ttc | ttt | ggt | 2999 |
| Thr | Gly | Ala | Gly | Gly | Gly | Leu | Gly | Lys | Ala | Tyr | Ala | Leu | Phe | Phe | Gly |
| 215 |  |  |  | 220 |  |  |  |  | 225 |  |  |  |  | 230 |

| gct | cgt | ggt | gca | tca | gtt | gtt | gtg | aat | gat | ctc | gga | ggc | aca | ttg | aat | 3047 |
|---|---|---|---|---|---|---|---|---|---|---|---|---|---|---|---|---|
| Ala | Arg | Gly | Ala | Ser | Val | Val | Val | Asn | Asp | Leu | Gly | Gly | Thr | Leu | Asn |
|  |  |  |  | 235 |  |  |  |  | 240 |  |  |  |  | 245 |  |

| ggt | ggt | gac | ggt | aac | tct | aga | gtt | gct | gat | gga | gtt | gta | aaa | gaa | att | 3095 |
|---|---|---|---|---|---|---|---|---|---|---|---|---|---|---|---|---|
| Gly | Gly | Asp | Gly | Asn | Ser | Arg | Val | Ala | Asp | Gly | Val | Val | Lys | Glu | Ile |
|  |  |  | 250 |  |  |  |  | 255 |  |  |  |  | 260 |  |  |

| gag | gct | ctt | gga | ggc | aaa | gca | gcg | gca | aat | tac | gat | agc | gtc | gag | aat | 3143 |
|---|---|---|---|---|---|---|---|---|---|---|---|---|---|---|---|---|
| Glu | Ala | Leu | Gly | Gly | Lys | Ala | Ala | Ala | Asn | Tyr | Asp | Ser | Val | Glu | Asn |
|  |  |  |  | 265 |  |  |  |  | 270 |  |  |  |  | 275 |  |

| ggt | gac | aag | atc | gtt | gaa | acc | gct | atc | aaa | gca | ttc | ggc | acg | gta | cac | 3191 |
|---|---|---|---|---|---|---|---|---|---|---|---|---|---|---|---|---|
| Gly | Asp | Lys | Ile | Val | Glu | Thr | Ala | Ile | Lys | Ala | Phe | Gly | Thr | Val | His |
|  | 280 |  |  |  |  | 285 |  |  |  |  | 290 |  |  |  |  |

| att | atc | atc | aat | aac | gca | gga | att | ctt | cgt | gac | gtc | agt | cta | aaa | aag | 3239 |
|---|---|---|---|---|---|---|---|---|---|---|---|---|---|---|---|---|
| Ile | Ile | Ile | Asn | Asn | Ala | Gly | Ile | Leu | Arg | Asp | Val | Ser | Leu | Lys | Lys |
| 295 |  |  |  |  | 300 |  |  |  |  | 305 |  |  |  |  | 310 |

| atg | acg | gat | aag | gat | ttc | aac | ttt | gtc | cag | tct | gtc | cac | gtc | ttt | ggc | 3287 |
|---|---|---|---|---|---|---|---|---|---|---|---|---|---|---|---|---|
| Met | Thr | Asp | Lys | Asp | Phe | Asn | Phe | Val | Gln | Ser | Val | His | Val | Phe | Gly |
|  |  |  |  | 315 |  |  |  |  | 320 |  |  |  |  | 325 |  |

| tcg | tac | gcg | gtt | acg | agg | gct | gct | tgg | cct | tat | ttc | aaa | caa | cag | aag | 3335 |
|---|---|---|---|---|---|---|---|---|---|---|---|---|---|---|---|---|
| Ser | Tyr | Ala | Val | Thr | Arg | Ala | Ala | Trp | Pro | Tyr | Phe | Lys | Gln | Gln | Lys |
|  |  |  | 330 |  |  |  |  | 335 |  |  |  |  | 340 |  |  |

| ttc | ggt | cgt | gtg | atc | aac | acc | gca | agc | gca | gct | ggt | cta | tat | ggc | aac | 3383 |
|---|---|---|---|---|---|---|---|---|---|---|---|---|---|---|---|---|
| Phe | Gly | Arg | Val | Ile | Asn | Thr | Ala | Ser | Ala | Ala | Gly | Leu | Tyr | Gly | Asn |
|  |  | 345 |  |  |  |  | 350 |  |  |  |  | 355 |  |  |  |

| ttt | ggc | cag | gcc | aat | tat | tct | gcg | gct | aaa | tcc | gct | ttg | gtg | ggc | ttt | 3431 |
|---|---|---|---|---|---|---|---|---|---|---|---|---|---|---|---|---|
| Phe | Gly | Gln | Ala | Asn | Tyr | Ser | Ala | Ala | Lys | Ser | Ala | Leu | Val | Gly | Phe |
|  | 360 |  |  |  |  | 365 |  |  |  |  | 370 |  |  |  |  |

| act | gaa | act | ttg | gct | aaa | gag | ggc | gcc | aaa | tac | aat | atc | acc | gct | aac | 3479 |
|---|---|---|---|---|---|---|---|---|---|---|---|---|---|---|---|---|
| Thr | Glu | Thr | Leu | Ala | Lys | Glu | Gly | Ala | Lys | Tyr | Asn | Ile | Thr | Ala | Asn |
| 375 |  |  |  |  | 380 |  |  |  |  | 385 |  |  |  |  | 390 |

| gtt | att | gtt | cca | ctg | gcg | gcg | tcg | cgc | atg | act | gag | acc | att | ctt | cct | 3527 |
|---|---|---|---|---|---|---|---|---|---|---|---|---|---|---|---|---|
| Val | Ile | Val | Pro | Leu | Ala | Ala | Ser | Arg | Met | Thr | Glu | Thr | Ile | Leu | Pro |
|  |  |  |  | 395 |  |  |  |  | 400 |  |  |  |  | 405 |  |

| cct | gac | att | cta | gag | aag | ctg | aag | ccc | gag | ctc | atc | gtt | cct | gtt | gtc | 3575 |
|---|---|---|---|---|---|---|---|---|---|---|---|---|---|---|---|---|
| Pro | Asp | Ile | Leu | Glu | Lys | Leu | Lys | Pro | Glu | Leu | Ile | Val | Pro | Val | Val |
|  |  |  | 410 |  |  |  |  | 415 |  |  |  |  | 420 |  |  |

| gga | tac | ctc | gtt | cat | gag | aat | aca | gca | gag | agc | aat | gga | atc | tac | gaa | 3623 |
|---|---|---|---|---|---|---|---|---|---|---|---|---|---|---|---|---|
| Gly | Tyr | Leu | Val | His | Glu | Asn | Thr | Ala | Glu | Ser | Asn | Gly | Ile | Tyr | Glu |
|  |  | 425 |  |  |  |  | 430 |  |  |  |  | 435 |  |  |  |

| agt | gct | gct | ggc | gtt | gta | acc | aag | gtg | aga | tgg | cag | cgt | gga | gct | ggt | 3671 |
|---|---|---|---|---|---|---|---|---|---|---|---|---|---|---|---|---|
| Ser | Ala | Ala | Gly | Val | Val | Thr | Lys | Val | Arg | Trp | Gln | Arg | Gly | Ala | Gly |
|  | 440 |  |  |  |  | 445 |  |  |  |  | 450 |  |  |  |  |

| gta | cag | ttc | agg | gct | gat | gac | tcg | ttc | act | ccc | gct | gca | gtg | ttg | aac | 3719 |
|---|---|---|---|---|---|---|---|---|---|---|---|---|---|---|---|---|
| Val | Gln | Phe | Arg | Ala | Asp | Asp | Ser | Phe | Thr | Pro | Ala | Ala | Val | Leu | Asn |
| 455 |  |  |  |  | 460 |  |  |  |  | 465 |  |  |  |  | 470 |

| aaa | ttc | gaa | gaa | atc | aac | gac | aac | ttt | gag | cca | gca | gag | tac | ccc | agt | 3767 |
|---|---|---|---|---|---|---|---|---|---|---|---|---|---|---|---|---|
| Lys | Phe | Glu | Glu | Ile | Asn | Asp | Asn | Phe | Glu | Pro | Ala | Glu | Tyr | Pro | Ser |
|  |  |  |  | 475 |  |  |  |  | 480 |  |  |  |  | 485 |  |

| ggg | ccc | aag | gat | ctt | cta | gct | gcc | ttt | gaa | aat | ggc | aag | aat | ctg | cct | 3815 |
|---|---|---|---|---|---|---|---|---|---|---|---|---|---|---|---|---|
| Gly | Pro | Lys | Asp | Leu | Leu | Ala | Ala | Phe | Glu | Asn | Gly | Lys | Asn | Leu | Pro |
|  |  |  | 490 |  |  |  |  | 495 |  |  |  |  | 500 |  |  |

| tcg | aat | gag | cag | gga | agc | act | cca | gta | agt | ttc | gag | aac | cag | gtc | gtt | 3863 |
|---|---|---|---|---|---|---|---|---|---|---|---|---|---|---|---|---|
| Ser | Asn | Glu | Gln | Gly | Ser | Thr | Pro | Val | Ser | Phe | Glu | Asn | Gln | Val | Val |
|  |  | 505 |  |  |  |  | 510 |  |  |  |  | 515 |  |  |  |

| atc | gtt | act | ggt | gcg | gga | ggc | gga | att | gga | cag | caa | tat | gct | ctc | atg | 3911 |
|---|---|---|---|---|---|---|---|---|---|---|---|---|---|---|---|---|
| Ile | Val | Thr | Gly | Ala | Gly | Gly | Gly | Ile | Gly | Gln | Gln | Tyr | Ala | Leu | Met |

```
                520                 525                 530
ctc ggt aag ttg gga gcg aag gtt gtt gtg aat gac ctt ggc aac gct   3959
Leu Gly Lys Leu Gly Ala Lys Val Val Val Asn Asp Leu Gly Asn Ala
535                 540                 545                 550 gat gct acc gtg gaa ttg atc aag aag gct gga gga acg gct gtg gcg   4007
Asp Ala Thr Val Glu Leu Ile Lys Lys Ala Gly Gly Thr Ala Val Ala
                    555                 560                 565 gat aag cac aat gtc acc gat ggt gag gca gtt gtg aag act gct cta   4055
Asp Lys His Asn Val Thr Asp Gly Glu Ala Val Val Lys Thr Ala Leu
                570                 575                 580 gac aat ttc ggt gct atc cat gcg gtt atc aac aat gcc ggt atc att   4103
Asp Asn Phe Gly Ala Ile His Ala Val Ile Asn Asn Ala Gly Ile Ile
            585                 590                 595 cgt gat cgt ggc att ctc aag atg acg ccc gat ctc tgg aat gct gtt   4151
Arg Asp Arg Gly Ile Leu Lys Met Thr Pro Asp Leu Trp Asn Ala Val
600                 605                 610 caa cag gtt cat cta ttc ggt tcc ttt tca gtc acc aaa gct gca tgg   4199
Gln Gln Val His Leu Phe Gly Ser Phe Ser Val Thr Lys Ala Ala Trp
615                 620                 625                 630 cct cat ttc cag aag cag aaa tac gga cgt gtg gtc aac acg act tca   4247
Pro His Phe Gln Lys Gln Lys Tyr Gly Arg Val Val Asn Thr Thr Ser
                    635                 640                 645 acc tct gga atc tac gga aat ttc gga cag aca aac tac tca gcg gca   4295
Thr Ser Gly Ile Tyr Gly Asn Phe Gly Gln Thr Asn Tyr Ser Ala Ala
                650                 655                 660 aag gcc ggt ctc att ggc ttc acc aag act gtg gca cta gaa ggt gcc   4343
Lys Ala Gly Leu Ile Gly Phe Thr Lys Thr Val Ala Leu Glu Gly Ala
            665                 670                 675 aag tac aac att ctt tgc aac tgc gtt gcc cct aca gca gga act gct   4391
Lys Tyr Asn Ile Leu Cys Asn Cys Val Ala Pro Thr Ala Gly Thr Ala
680                 685                 690 atg act gct gat gtg ttc cct caa gat atg ctg gag acg ttg aag cca   4439
Met Thr Ala Asp Val Phe Pro Gln Asp Met Leu Glu Thr Leu Lys Pro
695                 700                 705                 710 agg tac att gcg cca atc act gtc ctg ctt gct agt gag cac tcg ccc   4487
Arg Tyr Ile Ala Pro Ile Thr Val Leu Leu Ala Ser Glu His Ser Pro
                    715                 720                 725 gac acc ggt aag gtc tac gaa gca ggt gct ggc tgg att ggc cgc acg   4535
Asp Thr Gly Lys Val Tyr Glu Ala Gly Ala Gly Trp Ile Gly Arg Thr
                730                 735                 740 cgt tgg cag aga act tcg ggt gtc atg att cct ggt atc aca gtg gaa   4583
Arg Trp Gln Arg Thr Ser Gly Val Met Ile Pro Gly Ile Thr Val Glu
            745                 750                 755 aag gtt aag caa aat tgg cag aaa atc acc gat ttc gat gac ggg aag   4631
Lys Val Lys Gln Asn Trp Gln Lys Ile Thr Asp Phe Asp Asp Gly Lys
760                 765                 770 gct acc aac ttt gag tcc gcc tcc gaa gca aac atg tac atc ttc aac   4679
Ala Thr Asn Phe Glu Ser Ala Ser Glu Ala Asn Met Tyr Ile Phe Asn
775                 780                 785                 790 atg gca gct gag ggc gaa gac caa ggc tct gaa ggt ggc gaa tct gag   4727
Met Ala Ala Glu Gly Glu Asp Gln Gly Ser Glu Gly Gly Glu Ser Glu
                    795                 800                 805 gct tca gca agc ggc gaa tat tct tac gac gac aag acg atc att ttg   4775
Ala Ser Ala Ser Gly Glu Tyr Ser Tyr Asp Asp Lys Thr Ile Ile Leu
                810                 815                 820 tac aac ttg gga gtt ggt gcg agc gag aag cag ctc aat tat act ttt   4823
Tyr Asn Leu Gly Val Gly Ala Ser Glu Lys Gln Leu Asn Tyr Thr Phe
            825                 830                 835 gaa aac aat cag gat ttc cag cca gtg ccg agt ttc ggc acc atc ccg   4871
Glu Asn Asn Gln Asp Phe Gln Pro Val Pro Ser Phe Gly Thr Ile Pro
```

```
                840             845             850
ctc ttc agc gct cca ttc cca ttt gat gaa gtt gtg ccc aat ttc aat    4919
Leu Phe Ser Ala Pro Phe Pro Phe Asp Glu Val Val Pro Asn Phe Asn
855                 860                 865                 870 cca atg aag ctc ctt cat gga gag caa tat ttg gag ttg aag aag tgg    4967
Pro Met Lys Leu Leu His Gly Glu Gln Tyr Leu Glu Leu Lys Lys Trp
                875                 880                 885 ccc att gcc cca gag gca acg ttg aag acc acg ggc aag ctt ctc gat    5015
Pro Ile Ala Pro Glu Ala Thr Leu Lys Thr Thr Gly Lys Leu Leu Asp
        890                 895                 900 ctt gca gac aag ggc aaa gct gct gta gcg atg gtg gaa tat atc tct    5063
Leu Ala Asp Lys Gly Lys Ala Ala Val Ala Met Val Glu Tyr Ile Ser
            905                 910                 915 gtc gat aag aat tct ggt gag cct gtg ttc ctc aac gtc atg tca aca    5111
Val Asp Lys Asn Ser Gly Glu Pro Val Phe Leu Asn Val Met Ser Thr
920                 925                 930 ttc ttg aga ggc tcc gga ggt ttc ggg ggt gag aag aat ttc aag gac    5159
Phe Leu Arg Gly Ser Gly Gly Phe Gly Gly Glu Lys Asn Phe Lys Asp
935                 940                 945                 950 cat ggc ccc atc aca gca gcc aac aag cca ccg gct cgc gag ccc gac    5207
His Gly Pro Ile Thr Ala Ala Asn Lys Pro Pro Ala Arg Glu Pro Asp
        955                 960                 965 tat atc gcc aag tac aag acc acg gac aac cag gct gca atc tat cga    5255
Tyr Ile Ala Lys Tyr Lys Thr Thr Asp Asn Gln Ala Ala Ile Tyr Arg
            970                 975                 980 cta tca gga gac tac aac cct ctt cac att gat cct gag ttt gct gcc    5303
Leu Ser Gly Asp Tyr Asn Pro Leu His Ile Asp Pro Glu Phe Ala Ala
                985                 990                 995 gtt ggc gga ttc gat cgt ccg att ctt cac ggc ctt gcg tct ttc        5348
Val Gly Gly Phe Asp Arg Pro Ile Leu His Gly Leu Ala Ser Phe
    1000            Gly     1005                1010 gga atc tca tca aga ttg ttg gtt gaa aag tat ggc gtt ttc aag        5393
Gly Ile Ser Ser Arg Leu Leu Val Glu Lys Tyr Gly Val Phe Lys
    1015                1020                1025 aac atc aag gta aga ttc tcg ggc cat gtg ttc cct ggt gag act        5438
Asn Ile Lys Val Arg Phe Ser Gly His Val Phe Pro Gly Glu Thr
    1030                1035                1040 ctg caa gtt tcc gct tgg aag gaa ggt ccc aag gtg att ttt gag        5483
Leu Gln Val Ser Ala Trp Lys Glu Gly Pro Lys Val Ile Phe Glu
    1045                1050                1055 acg acg gtg ctg gag cgt aac acc aaa gcc att act gca gca gca        5528
Thr Thr Val Leu Glu Arg Asn Thr Lys Ala Ile Thr Ala Ala Ala
    1060                1065                1070 att gag ctg gct gat gat ggt aag tct aag ctg tga cggagaagct         5574
Ile Glu Leu Ala Asp Asp Gly Lys Ser Lys Leu
    1075                1080 atatagttaa ataaataaga ttacaagtcg acttctgtca ggccagaggt gtaggttgcg  5634
ttcagaaacg caagtgcaga cttcttccta tcaaggtcct catacatgaa gtaagtatta  5694
gatttgaaaa gtacttgagc cacatctaaa ctcctcaaca ttgttcattc cataatacga  5754
gcaaaactgc tcctcggtca gtagagcct aaaattgatt ggaggaatat cgtctttcac   5814
aatgcgttgc ttcttagcct tgggaagcgg ggctgtcggg ttttgtctcg tgtagaactg  5874
gcgaagtaac aaaacagcct cttttctctt cagattggga attacatcgt atgatgaacc  5934
tattgactga ttaggcgtat ctcggttgat tgcgagtaca gaaccacatc caccgaaacg  5994
ctcatttccg gcgccaaagt aaaccttcct tatgctcac                         6033
```

<210> SEQ ID NO 2

-continued

```
<211> LENGTH: 200
<212> TYPE: PRT
<213> ORGANISM: Candida bombicola
<220> FEATURE:
<221> NAME/KEY: misc_feature
<222> LOCATION: (149)..(149)
<223> OTHER INFORMATION: The 'Xaa' at location 149 stands for Ala, or
      Ser.

<400> SEQUENCE: 2

Met Gly Ala Leu Ala Tyr Ser Leu Leu Gly Leu Ser Ala Leu Ala Ala
1               5                   10                  15

Val Val Ala Gly Ser Tyr Ala Leu Phe Thr Gly Gln Gly Ser Gln Phe
            20                  25                  30

Asp Val Gly His Phe Leu Leu Thr Thr Ser Pro Phe Met Trp Ala Leu
        35                  40                  45

Leu Gly Val Pro Leu Cys Thr Gly Leu Ser Ile Ala Gly Ala Ala Trp
    50                  55                  60

Gly Ile Phe Ile Thr Gly Thr Ser Ile Leu Gly Ala Ser Val Lys Val
65                  70                  75                  80

Pro Arg Val Thr Thr Lys Asn Leu Val Ser Val Phe Cys Glu Val
                85                  90                  95

Val Ala Ile Phe Gly Leu Ile Thr Ser Ile Val Leu Ser Ser Lys Ile
                100                 105                 110

Ser Ser Thr Gly Phe Asn Thr Ala Leu Ser Lys Glu Asn Leu Phe Thr
            115                 120                 125

Gly Tyr Ala Val Phe Trp Ala Gly Leu Thr Val Gly Val Ser Asn Leu
        130                 135                 140

Val Cys Gly Val Xaa Val Gly Val Ala Gly Thr Ala Ala Val Ser
145                 150                 155                 160

Asp Ala Ala Asp Pro Ser Leu Phe Val Lys Ile Leu Val Ile Glu Ile
                165                 170                 175

Phe Gly Ser Val Ile Gly Leu Phe Gly Leu Ile Val Gly Leu Leu Met
            180                 185                 190

Ser Thr Glu Ala Pro Glu Phe Ser
        195                 200

<210> SEQ ID NO 3
<211> LENGTH: 884
<212> TYPE: PRT
<213> ORGANISM: Candida bombicola

<400> SEQUENCE: 3

Met Ala Glu Asn Leu Arg Tyr Asp Gly Lys Val Val Val Thr Gly
1               5                   10                  15

Ala Gly Gly Gly Leu Gly Lys Ala Tyr Ala Leu Phe Phe Gly Ala Arg
            20                  25                  30

Gly Ala Ser Val Val Val Asn Asp Leu Gly Gly Thr Leu Asn Gly Gly
        35                  40                  45

Asp Gly Asn Ser Arg Val Ala Asp Gly Val Val Lys Glu Ile Glu Ala
    50                  55                  60

Leu Gly Gly Lys Ala Ala Ala Asn Tyr Asp Ser Val Glu Asn Gly Asp
65                  70                  75                  80

Lys Ile Val Glu Thr Ala Ile Lys Ala Phe Gly Thr Val His Ile Ile
                85                  90                  95

Ile Asn Asn Ala Gly Ile Leu Arg Asp Val Ser Leu Lys Lys Met Thr
                100                 105                 110

Asp Lys Asp Phe Asn Phe Val Gln Ser Val His Val Phe Gly Ser Tyr
```

```
                115                 120                 125
    Ala Val Thr Arg Ala Ala Trp Pro Tyr Phe Lys Gln Gln Lys Phe Gly
    130                 135                 140

Arg Val Ile Asn Thr Ala Ser Ala Ala Gly Leu Tyr Gly Asn Phe Gly
145                 150                 155                 160

Gln Ala Asn Tyr Ser Ala Ala Lys Ser Ala Leu Val Gly Phe Thr Glu
                    165                 170                 175

Thr Leu Ala Lys Glu Gly Ala Lys Tyr Asn Ile Thr Ala Asn Val Ile
                180                 185                 190

Val Pro Leu Ala Ala Ser Arg Met Thr Glu Thr Ile Leu Pro Pro Asp
                195                 200                 205

Ile Leu Glu Lys Leu Lys Pro Glu Leu Ile Val Pro Val Val Gly Tyr
    210                 215                 220

Leu Val His Glu Asn Thr Ala Glu Ser Asn Gly Ile Tyr Glu Ser Ala
    225                 230                 235                 240

Ala Gly Val Val Thr Lys Val Arg Trp Gln Arg Gly Ala Gly Val Gln
                    245                 250                 255

Phe Arg Ala Asp Asp Ser Phe Thr Pro Ala Ala Val Leu Asn Lys Phe
                260                 265                 270

Glu Glu Ile Asn Asp Asn Phe Glu Pro Ala Glu Tyr Pro Ser Gly Pro
                275                 280                 285

Lys Asp Leu Leu Ala Ala Phe Glu Asn Gly Lys Asn Leu Pro Ser Asn
    290                 295                 300

Glu Gln Gly Ser Thr Pro Val Ser Phe Glu Asn Gln Val Val Ile Val
305                 310                 315                 320

Thr Gly Ala Gly Gly Gly Ile Gly Gln Gln Tyr Ala Leu Met Leu Gly
                    325                 330                 335

Lys Leu Gly Ala Lys Val Val Asn Asp Leu Gly Asn Ala Asp Ala
                340                 345                 350

Thr Val Glu Leu Ile Lys Lys Ala Gly Gly Thr Ala Val Ala Asp Lys
                355                 360                 365

His Asn Val Thr Asp Gly Glu Ala Val Val Lys Thr Ala Leu Asp Asn
    370                 375                 380

Phe Gly Ala Ile His Ala Val Ile Asn Asn Ala Gly Ile Ile Arg Asp
385                 390                 395                 400

Arg Gly Ile Leu Lys Met Thr Pro Asp Leu Trp Asn Ala Val Gln Gln
                    405                 410                 415

Val His Leu Phe Gly Ser Phe Ser Val Thr Lys Ala Ala Trp Pro His
                420                 425                 430

Phe Gln Lys Gln Lys Tyr Gly Arg Val Val Asn Thr Thr Ser Thr Ser
                435                 440                 445

Gly Ile Tyr Gly Asn Phe Gly Gln Thr Asn Tyr Ser Ala Ala Lys Ala
                450                 455                 460

Gly Leu Ile Gly Phe Thr Lys Thr Val Ala Leu Glu Gly Ala Lys Tyr
465                 470                 475                 480

Asn Ile Leu Cys Asn Cys Val Ala Pro Thr Ala Gly Thr Ala Met Thr
                    485                 490                 495

Ala Asp Val Phe Pro Gln Asp Met Leu Glu Thr Leu Lys Pro Arg Tyr
                500                 505                 510

Ile Ala Pro Ile Thr Val Leu Leu Ala Ser Glu His Ser Pro Asp Thr
                515                 520                 525

Gly Lys Val Tyr Glu Ala Gly Ala Gly Trp Ile Gly Arg Thr Arg Trp
    530                 535                 540
```

```
Gln Arg Thr Ser Gly Val Met Ile Pro Gly Ile Thr Val Glu Lys Val
545                 550                 555                 560

Lys Gln Asn Trp Gln Lys Ile Thr Asp Phe Asp Gly Lys Ala Thr
            565                 570                 575

Asn Phe Glu Ser Ala Ser Glu Ala Asn Met Tyr Ile Phe Asn Met Ala
            580                 585                 590

Ala Glu Gly Glu Asp Gln Gly Ser Glu Gly Gly Glu Ser Glu Ala Ser
            595                 600                 605

Ala Ser Gly Glu Tyr Ser Tyr Asp Asp Lys Thr Ile Ile Leu Tyr Asn
610                 615                 620

Leu Gly Val Gly Ala Ser Glu Lys Gln Leu Asn Tyr Thr Phe Glu Asn
625                 630                 635                 640

Asn Gln Asp Phe Gln Pro Val Pro Ser Phe Gly Thr Ile Pro Leu Phe
            645                 650                 655

Ser Ala Pro Phe Pro Phe Asp Glu Val Val Pro Asn Phe Asn Pro Met
            660                 665                 670

Lys Leu Leu His Gly Glu Gln Tyr Leu Glu Leu Lys Lys Trp Pro Ile
            675                 680                 685

Ala Pro Glu Ala Thr Leu Lys Thr Thr Gly Lys Leu Leu Asp Leu Ala
            690                 695                 700

Asp Lys Gly Lys Ala Ala Val Ala Met Val Glu Tyr Ile Ser Val Asp
705                 710                 715                 720

Lys Asn Ser Gly Glu Pro Val Phe Leu Asn Val Met Ser Thr Phe Leu
            725                 730                 735

Arg Gly Ser Gly Gly Phe Gly Gly Glu Lys Asn Phe Lys Asp His Gly
            740                 745                 750

Pro Ile Thr Ala Ala Asn Lys Pro Pro Ala Arg Glu Pro Asp Tyr Ile
            755                 760                 765

Ala Lys Tyr Lys Thr Thr Asp Asn Gln Ala Ala Ile Tyr Arg Leu Ser
770                 775                 780

Gly Asp Tyr Asn Pro Leu His Ile Asp Pro Glu Phe Ala Ala Val Gly
785                 790                 795                 800

Gly Phe Asp Arg Pro Ile Leu His Gly Leu Ala Ser Phe Gly Ile Ser
            805                 810                 815

Ser Arg Leu Leu Val Glu Lys Tyr Gly Val Phe Lys Asn Ile Lys Val
            820                 825                 830

Arg Phe Ser Gly His Val Phe Pro Gly Glu Thr Leu Gln Val Ser Ala
            835                 840                 845

Trp Lys Glu Gly Pro Lys Val Ile Phe Glu Thr Thr Val Leu Glu Arg
            850                 855                 860

Asn Thr Lys Ala Ile Thr Ala Ala Ala Ile Glu Leu Ala Asp Asp Gly
865                 870                 875                 880

Lys Ser Lys Leu

<210> SEQ ID NO 4
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: primer MFE2_3545For (cloning MFE2)

<400> SEQUENCE: 4
ctcctaagca tttaactgcc ttgag                                                25
```

```
<210> SEQ ID NO 5
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: primer MFE2_3545Rev (cloning MFE2)

<400> SEQUENCE: 5
aaccgagata cgcctaatca gtc                                            23

<210> SEQ ID NO 6
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(34)
<223> OTHER INFORMATION: primer URA3infMFE2For (ligating Ura3 into MFE2)

<400> SEQUENCE: 6
tgcgttgccc ctacactgac gggcggatag taca                                34

<210> SEQ ID NO 7
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(34)
<223> OTHER INFORMATION: primer URA3inf MFE2Rev (ligating Ura3 into
      MFE2)

<400> SEQUENCE: 7
tggtcttcgc cctcacatca tcgtcactat acac                                34

<210> SEQ ID NO 8
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: primer MFE2knock1000For (4095 bp knock-out
      fragment)

<400> SEQUENCE: 8
ggcaactttg gccaggccaa tta                                            23

<210> SEQ ID NO 9
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: primer MFE2knock1000Rev (4095 bp knock-out
      fragment)
```

```
-continued

<400> SEQUENCE: 9
gtttagatgt ggctcaagta                                                   20

<210> SEQ ID NO 10
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: primer MFE2knock500For (3070 bp knock-out
      fragment)

<400> SEQUENCE: 10
tactggtgcg ggaggcggaa ttg                                               23

<210> SEQ ID NO 11
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: primer MFE2knock500Rev (3070 bp knock-out
      fragment)

<400> SEQUENCE: 11
ggtggcttgt tggctgctgt gat                                               23
```